US012121327B2

(12) United States Patent
Attia et al.

(10) Patent No.: US 12,121,327 B2
(45) Date of Patent: *Oct. 22, 2024

(54) ECG-BASED CARDIAC EJECTION-FRACTION SCREENING

(71) Applicant: Mayo Foundation for Medical Education and Research, Rochester, MN (US)

(72) Inventors: Itzhak Zachi Attia, Rochester, MN (US); Paul A. Friedman, Rochester, MN (US); Francisco Lopez-Jimenez, Rochester, MN (US); Suraj Kapa, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/053,200

(22) Filed: Nov. 7, 2022

(65) Prior Publication Data
US 2023/0089991 A1 Mar. 23, 2023

Related U.S. Application Data

(63) Continuation of application No. 16/754,007, filed as application No. PCT/US2018/054371 on Oct. 4, 2018.
(Continued)

(51) Int. Cl.
*A61B 5/00* (2006.01)
*A61B 5/02* (2006.01)
(Continued)

(52) U.S. Cl.
CPC .......... *A61B 5/02028* (2013.01); *A61B 5/316* (2021.01); *A61B 5/352* (2021.01);
(Continued)

(58) Field of Classification Search
None
See application file for complete search history.

(56) References Cited

U.S. PATENT DOCUMENTS 4,245,646 A 1/1981 Ionnou et al.
9,737,229 B1 * 8/2017 Gupta ................. A61B 5/1075
(Continued)

FOREIGN PATENT DOCUMENTS

WO 2012058521 A1 5/2012
WO 2015058044 A1 4/2015

OTHER PUBLICATIONS

Di Salvo, T. G., Mathier, M., Semigran, M. J., & Dec, G. W. (1995). Preserved right ventricular ejection fraction predicts exercise capacity and survival in advanced heart failure. Journal of the American College of Cardiology, 25(5), 1143-1153 (Year: 1995).*

(Continued)

*Primary Examiner* — John R Downey
*Assistant Examiner* — Anant A Gupta
(74) *Attorney, Agent, or Firm* — Caldwell Intellectual Property Law

(57) ABSTRACT

Systems, methods, devices, and techniques for estimating a heart disease prediction of a mammal. An electrocardiogram (ECG) procedure is performed on a mammal, and a computer system obtains ECG data that describes results of the ECG over a period of time. The system provides a predictive input that is based on the ECG data to a predictive model, such as a neural network or other machine-learning model. In response, the predictive model processes the input to generate an estimated heart disease predictive characteristic of the mammal. The system outputs the estimated heart disease prediction of the mammal for presentation to a user.

17 Claims, 17 Drawing Sheets

Related U.S. Application Data

(60) Provisional application No. 62/599,163, filed on Dec. 15, 2017, provisional application No. 62/569,268, filed on Oct. 6, 2017.

(51) Int. Cl.

| | |
|---|---|
| *A61B 5/316* | (2021.01) |
| *A61B 5/352* | (2021.01) |
| *A61B 5/366* | (2021.01) |
| *G06N 3/04* | (2023.01) |
| *G06N 20/00* | (2019.01) |
| *G16H 40/67* | (2018.01) |
| *G16H 50/20* | (2018.01) |

(52) U.S. Cl.
CPC ............... *A61B 5/366* (2021.01); *G06N 3/04* (2013.01); *G06N 20/00* (2019.01); *G16H 40/67* (2018.01); *G16H 50/20* (2018.01)

(56) References Cited

U.S. PATENT DOCUMENTS

| | | | | |
|---|---|---|---|---|
| 2008/0269813 | A1* | 10/2008 | Greenhut | A61N 1/0504 607/36 |
| 2009/0112113 | A1 | 4/2009 | Mukkamala | |
| 2009/0287070 | A1* | 11/2009 | Baker, Jr. | G16Z 99/00 600/324 |
| 2011/0021933 | A1* | 1/2011 | Radzievsky | G16H 40/63 600/509 |
| 2013/0165776 | A1* | 6/2013 | Blomqvist | A61B 5/1107 600/509 |
| 2014/0276164 | A1* | 9/2014 | Thakur | A61N 1/36139 600/528 |
| 2015/0133803 | A1 | 5/2015 | Gupta et al. | |
| 2015/0216426 | A1* | 8/2015 | Burton | A61B 5/7275 600/509 |
| 2016/0000349 | A1 | 1/2016 | Sullivan et al. | |
| 2017/0188978 | A1* | 7/2017 | Kale | A61B 5/02028 |
| 2017/0347899 | A1* | 12/2017 | Bhushan | A61B 5/6833 |
| 2020/0397313 | A1 | 12/2020 | Attia et al. | |

OTHER PUBLICATIONS

Attia et al., Automated detection of low ejection fraction from a one-lead electrocardiogram: application of an AI algorithm to an electrocardiogram-enabled Digital Stethoscope, European Heart Journal, May 23, 2022, 373-379, 3, European Society of Cardiology.

Ko et al., Detection of HypertrophicCardiomyopathy Using aConvolutional NeuralNetwork-Enabled Electrocardiogram, Journal of the American College of Cardiology, Feb. 25, 2020, 722-733, vol. 75 No. 7, Amercian College of Cardiology.

Yoshida et al., "Automated histological classification of whole-slide images of gastric biopsy specimens," Gastric Cancer, ,Jun. 2, 2017, 21(2)249-257.

Yasin et al., "Noninvasive Blood Potassium Measurement Using Signal-Processed, Single-Lead ECG Acquired from a Handheld Smartphone," J. Electrocardiology, Sep./Oct. 2017, 50(5):620-625.

Yancy et al., "2017 ACC/AHA/HFSA Focused Update of the 2013 ACCF/AHA Guideline for the Management of Heart Failure: A Report of the American College of Cardiology/American Heart Association Task Force on Clinical Practice Guidelines and the Heart Failure Society of America," J. Am. Coll. Cardiology, Aug. 8, 2017, 70(6):776-803.

Yancy et al., "2016 ACC/AHA/HFSA Focused Update on New Pharmacological Therapy for Heart Failure: An Update of the 2013 ACCF/AHA Guideline for the Management of Heart Failure," Circulation, Sep. 27, 2016; 134(13):e282-e293.

Yancy et al., "2013 ACCF/AHA Ch1ideline for the Management off Heart Failure: A Report o.fthe American College of Cardiology Foundation/American Heart Association Task Force on Practice Guidelines," J. A1n. Coll. Cardiology., Nov. 16, 2013, 62(16):e147-e239.

Yancy et al., "2013 ACCF/AHA Guideline for the Management of Heart Failure: A Report of the American College of Cardiology Foundation/American Heart Association Task Force on Practice. Guidelines," Circulation, Oct. 15, 2013, 128(16):e240-e327.

Yantani et al., "Three-Dimensional Echocardiography in Evaluation of Left Ventricular Indices," Echocardiography, Jan. 2012, 29(1):66-75.

Wingfield et al., "Relating dynamic brain states to dynamic machine states: Human and machine solutions to the speech recognition problem," PLOS Comput. Biology, Sep. 25, 2017, 13:el005617, 25 pages.

Wilson et al., "Principles and Practice of Screening for Disease," Public Health Papers, 1968., 34, 168 pages.

van Rossum, "Python Tutorial: Technical Report CS-R9526," Version 1.2, Apr. 10, 1995, 71 pages.

Towardsdatascience.com [online], Support Vector Machine—Introduction to Machine Learning Algorithms, Jun. 7, 2018, retrieved on Feb. 12, 2021.

Stramba-Badiale et al., "Gender and the relationship between ventricular repolarization and cardiac cycle length during 24-h Holter recordings," Em. Heart Journal, Jun. 1997, 18(6):1000-1006.

Salazar-Licea et al., "Location of mammograms ROI's and reduction of false positive," Comput. Methods Programs Biomedicine, May 2017, 143:97-111.

Russo et al., "ACCF/HRS/AHA/ASE/HFSA/SCAI/SCCT/SCMR 2013 Appropriate Use Criteria for Implantable Cardioverter-Defibrillators and Cardiac Resynchronization Therapy: A Report of the American College of Cardiology Foundation Appropriate Use Criteria Task Force, Heart Rhythm Society, American Heart Association, American Society of Echocardiography, Heart Failure Society of America, Resonance.," J. Am. Coll. Cai:diology, March 2(-i, 2013, 61(12):1318-1368.

Redfield et al., "Plasma Brain Natriuretic Peptide to Detect Preclinical Ventricular Systolic or Diastolic Dvsfunction: A Comnnmitv-Based St1:1dv," Circulation, Jun. 29, 2004, 109(25):3176-3181.

Quinones er al., "A New, Simplified and Accurate Method for Determining Ejection fraction with Two-dimensional Echocardiography," Circulation. Oct. 1981, 64(4):744-753.

Priori et al., "2015 ESC Guidelines for the management of patients with ventricular arrhythmias and tl1e prevention of sudden cardiac death: The Task Force for the Management of Patients with Ventricular Arrhythmias and the Prevention of Sudden Cardiac Death of the European Society of Cardiology (ESC)," Eur. Heart Journal, Nov. 2015, 36( 41) :2 79 3-2 867.

Pfeffer et al., "Effect of Captopril on Mortality and Morbidity in Patients with Left Ventricular Dysfunction After Myocardial Infarction: Results of the Survival and Ventricular Enlargement Trial," N. Engl. J. Medicine, Sep. 3, 1992. 327(10:669-677.

Pasquier et al., "Ft.1zzylot: a novel self-organizing fuzzy-neural rule-based pilot system for automated vehicles," Neural Networks. October 200 I, 14(8): 1 099-1112.

Nagi et al., "Max-pooling convolutional neural networks for vision-based hand gesture recognition," 2011 IEEE International Conference on Signal and Image Processing Applications, Kuala Lumpur, Malaysia. Nov. 16-18, 2011, 342-347.

Mozaffarian et al., "Heart Disease and Stroke Statistics—2015 Update: A Report From the American Heart Association, " Circulation,. Jan. 27, 2015, I 3 I {4);e29-e322.

McDonagh et al., "Screening for Asymptomatic Left Ventricular Dysfunction Using B-Type Natriuretic Peptide," Congest. Heart Failure, Jul./Aug. 2008, 14( 4 Supp] I) 5-8.

Kuo et al.. "Effect of aging on gender differences in neural control of heart rate," Am. J. Physiology, Dec. 1999, 277(6):H2233-H2239.

Kingma et al., "Adam: A Method for Stochastic Optimization," arXiv, Dec. 22, 2014, arXiv:1412.6980vl, 9 pages.

Kim et al., "Evaluating a Pivot-Based Approach for Bilingual Lexicon Extraction," Comput. Intell. Neuroscience, May 2015, 2015(5):434153, 13 pages.

Khane e.t al., "Changes in ECG pattern with advancing age," J. Basic Clin. Physiol. Pharmacology, Sep. 2011, 22(4):97-IOI.

(56) References Cited

OTHER PUBLICATIONS

Ioffe et al., "Batch Normalization: Accelerating Deep Network Training by Machine Reducing Learning, Internal Jul. 2015, Covariate shift. "Proceedings of the 32nd International Conference on Machine Learning, Jul. 2015, 37:448-456.

Heidenreich et al., Heart "Forecasting the Impact of Heart Failure in the United States: A Policy Statement from the American Heart Association, "Circ. Heart Failure, May 2013.

Gruca et al., "Providing Cardiology Care in Rural Areas Through Visiting Consultant Clinics, "J.Am. Heart. Association. Jun. 30, 2016.

Dargie, "Effect of carvedilol on outcome after myocardial infraction in patients with left-ventricular dysfunction: the CAPRICORN randomized trial," May 5, 2001.

Daly Circulation, et al. "Gender Differences in the Management and Clinical Outcome of Stable Angina,"Jan. 31, Differences 2006.

Bhalla Testing et al., Identify "Diagnostic Left Ability Ventricular of B-Type Natriuretic Peptide and Impedance Cardiography. Testing to Identify Left Ventricular Dysfunction in Hypertensive Patients." Am. J. Hypertension, Feb. 2005.

Betti Screening et al., The Asymptomatic Role Left of N-terminal,PRO-Brain Natriuretic in a Peptide and Echocardiography for Screening Asymptomatic Left Ventricular Dysfunction in a Population at High Risk for Heart Failure. Jun. 2009.

Al-Khatib et al., "201 7 AHA/ACC/HRS Guideline FOR Management of Patients With Ventricular Arrhythmias and the Prevention of Sudden Cardiac Death: Executive Summary." Sep. 25, 2018.

\* cited by examiner

Characteristics at First Echo-ECG

| Variable | Training Set (N=35970) | Validation Set (N=8989) | Test Set (N=52870) | P Value |
|---|---|---|---|---|
| Age | 61.6 (16.5) | 61.8 (16.5) | 61.8 (16.5) | 0.44 |
| Age groups n (%) | | | | 0.86 |
| <40 | 4,046 (11%) | 1,008 (11%) | 5,861 (11%) | |
| 40-49 | 3,875 (11%) | 942 (10%) | 5,599 (11%) | |
| 50-59 | 6,376 (18%) | 1,587 (18%) | 9,341 (18%) | |
| 60-69 | 8,559 (24%) | 2,110 (23%) | 12,649 (24%) | |
| 70-79 | 8,573 (24%) | 2,158 (24%) | 12,550 (24%) | |
| 80+ | 4,541 (13%) | 1,184 (13%) | 6,870 (13%) | |
| Sex, n (%) | | | | 0.64 |
| Female | 15,358 (43%) | 3,821 (43%) | 22,704 (43%) | |
| Male | 20,612 (57%) | 5,168 (57%) | 30,166 (57%) | |
| Mean Ejection Fraction | 56.3 (11.9) | 56.1 (12.1) | 56.2 (12.0) | 0.45 |
| Heart Failure | 10,365 (20%) | 7,003 (19%) | 1,803 (20%) | 0.45 |
| Diabetes Mellitus, n (%) | 8,458 (24%) | 2,079 (23%) | 12,433 (24%) | 0.71 |
| Hypercholesterole, n (%) | 15,593 (43%) | 3,851 (43%) | 23,059 (44%) | 0.35 |
| Renal Disease, n (%) | 6,929 (19%) | 1,685 (19%) | 10,219 (19%) | 0.43 |
| Hypertension, n (%) | 16,831 (47%) | 4,163 (46%) | 24,643 (47%) | 0.69 |
| Coronary Artery Disease, n (%) | 13,563 (38%) | 3,380 (38%) | 20,040 (38%) | 0.77 |
| Myocardial Infarction, n (%) | 4,556 (13%) | 1,111 (12%) | 6,770 (13%) | 0.48 |

FIG. 16

ECG-BASED CARDIAC EJECTION-FRACTION SCREENING

CROSS-REFERENCE TO RELATED APPLICATIONS

This application is a continuation of and claims priority to U.S. Non-provisional patent application Ser. No. 16/754,007, filed on Apr. 6, 2020, which is a section 371 of International Application No. PCT/US18/54371, which claims the benefit of priority to U.S. Provisional Application Ser. No. 62/569,268, filed on Oct. 6, 2017, and U.S. Provisional Application Ser. No. 62/599,163, filed on Dec. 15, 2017. The disclosures of the prior applications are considered part of the disclosure of this application, and is incorporated in their entirety into this application.

TECHNICAL FIELD

This document describes computer-based technology for analyzing physiological electrical data (e.g., electrocardiogram data), such as to estimate a structural heart disease characteristic of a patient.

BACKGROUND

Ejection fraction is a key measure of cardiac health in humans and other mammals. Ejection fraction generally indicates the amount of blood ejected from the heart by each pump. With each pumping cycle (i.e., a "beat" or "cardiac cycle"), the heart muscle contracts and relaxes to push blood through the arterial system of a subject. As the heart relaxes, the ventricles are filled with blood. A portion of the blood is then pumped from the ventricles through the aorta and to the arterial system during the contraction phase of the pumping cycle. Not all of the blood that filled the ventricles during relaxation can be pumped out during contraction, however. The percentage of blood that actually is ejected from the ventricles during a pumping cycle is referred to as the ejection fraction. Although ejection fraction often relates only to the measurement of the fraction of blood ejected from the left ventricle, for purposes of this specification, ejection fraction can alternatively refer to the fraction of blood ejected from the left ventricle alone, the right ventricle alone, or both ventricles indicative of heart muscle strength or health.

An ejection fraction of greater than about 50-55 percent is generally considered normal for humans. Some individuals, however, suffer (often unknowingly) from low ejection fraction, e.g., at or below the 50-55 percent range, or very low ejection fraction, e.g., at or below 35-percent. This is termed asymptomatic ventricular dysfunction (ASVD). Low or very low ejection fraction is often a marker for serious cardiac complications such as cardiac arrest, sudden death, and various stages of heart failure. Effective therapies exist to treat ASVD or to prevent these complications, when ASVD is diagnosed.

Ejection fraction has traditionally been measured using echocardiograms. During an echocardiogram, a sonographer uses a sound-wave transducer to generate images of the heart using specialized techniques. Echocardiograms are non-invasive, but often require a specialist to perform and to interpret the procedure, expensive equipment and infrastructure, typically in the lab of a patient's healthcare provider. Ejection fraction has also been measured using magnetic resonance imaging (MRI) techniques, computerized tomography (CT) techniques, and nuclear medicine scans. All of these require specially trained personnel and expensive equipment.

SUMMARY

This specification discloses systems, methods, devices, and other techniques for estimating the cardiac ejection fraction of a mammal from an electrocardiogram (ECG). An electrocardiogram is a measurement of the electrical activity of a mammal's heart. The pumping action of the heart is driven by the continuous cycle of electrical polarization and de-polarization of the heart muscle. This electrical activity can be captured by an electrocardiogram, whereby electrodes are placed on the surface of a subject (e.g., on the subject's chest and limbs) and the electrical potential is measured over a period of time between pairs of electrodes. The electrical signal captured by this process forms an electrocardiogram. When the electrocardiogram is plotted to show the variance in electrical potential between electrodes over time, a waveform or ECG tracing can be seen that shows the heart's polarization and de-polarization in each of one or more cardiac cycles. For the purposes of this specification, an electrocardiogram may include the traditional 12 leads, additional leads, or any number of leads to as few as a single lead. Additionally, the ECG may be acquired from adhesive electrodes, conductive electrodes, capacitive electrodes, handheld electrodes, worn/garment electrodes, subcutaneous electrodes, electrodes affixed to implanted devices or any combination thereof.

The shape of the ECG waveform is influenced by a number of factors. The techniques disclosed herein are premised in part on the recognition that a subject's ECG can be influenced by cardiac ejection fraction. For example, subtle deformations may be imparted on one or more portions of the ECG waveform for a subject who has low or very low ejection fraction as compared to another subject who has normal ejection fraction. The underlying disease affecting the heart, whether due to atherosclerosis, myopathic processes, inflammation, valvular derangements from any cause, can impair the heart muscle's pumping capability. The underlying disease can similarly affect the metabolism of individual myocytes or their interconnections, and lead to deposition of fibrosis or infiltration of inflammatory cells, all of which lead to subtle electrical changes. These local cardiac electrical changes contribute to deformations recorded on the surface ECG. Such deformations may not be visible with the naked eye, but may nonetheless be detectable using computer-based models according to the techniques disclosed herein. Accordingly, this specification describes how a subject's ECG may be used as a screening tool to predict an ejection fraction characteristic of the subject. In many scenarios, ECG-based screening may be preferable to measuring ejection fraction by echocardiogram or other means. ECG equipment is often more widely available then echocardiogram equipment, and can be performed more quickly without a trained sonographer. Moreover, consumer and home-based ECG equipment (e.g., single-lead ECG patches) are becoming increasingly prevalent. Using the techniques disclosed herein, ECG equipment in a variety of settings, whether clinical or home-based, may be used to increase the number of people screened for low ejection fraction and the frequency of screenings. In some cases, if a subject's ECG-screen indicates a sufficient likelihood of low or very low ejection fraction, further evaluation of the condition may be performed to verify the condition, e.g., by using other measurement means such as echocardiograms, MRIs, or CT scans.

The subject matter disclosed herein includes a computer-implemented method. The method can be performed by a system of one or more computers in one or more locations. In some aspects, the system has one or more processors and one or more computer-readable media encoded with instructions that, when executed by the one or more processors, cause the processors to perform the method. Some aspects include just the computer-readable media encoded with instructions that cause performance of the method when executed.

The method can include receiving, by the system, electrocardiogram (ECG) data that describes an ECG of a mammal over a period of time. The system provides a predictive input that was derived from the ECG data to an ejection-fraction predictive model. The predictive input can be processed using the ejection-fraction predictive model to generate an estimated ejection-fraction characteristic of the mammal. The system then provides, for output, the estimated ejection-fraction characteristic of the mammal.

These and other implementations can optionally further include one or more of the following features.

The ECG data can include one or more channels, each channel including a subset of the ECG data that describes a respective lead of the ECG of the mammal over the period of time. The predictive input can characterize the respective leads of the ECG for each of the one or more channels of the ECG data.

The ECG data can include multiple channels, each channel including a subset of the ECG data that describes a respective one of multiple leads of the ECG of the mammal over the period of time. The predictive input can characterize the multiple leads of the ECG for each of the multiple channels of the ECG data.

The period of time over which the ECG data describes the ECG of the mammal can span multiple cardiac cycles of the mammal.

The mammal can be a human.

The ejection-fraction predictive model can be a regression model, e.g., a logistic regression model.

The ejection-fraction predictive model can be a machine-learning model, such as a neural network (e.g., a feedforward neural network, a convolutional neural network, or a recurrent neural network).

The ejection-fraction model may use as inputs clinical characteristics (including age, gender, weight, and/or presence of measurable disease conditions such as hypertension and diabetes) to further refine its outputs.

The ejection fraction model may also generate additional outputs such as risk of death over a determined time period (e.g. risk of death over the next year).

The estimated ejection-fraction characteristic of the mammal can be a value that represents an absolute (e.g., specific) estimate of the ejection-fraction of the mammal.

The estimated ejection-fraction characteristic of the mammal can indicate an estimated range of the ejection-fraction of the mammal.

Providing, for output, the estimated ejection-fraction characteristic of the mammal can include providing the estimated ejection-fraction characteristic for presentation to the mammal or a healthcare provider associated with the mammal.

The method can further include generating the predictive input by determining values for one or more morphological features of the ECG of the mammal. The predictive input can indicate the values for the one or more morphological features of the ECG of the mammal.

The morphological features of the ECG of the mammal can include at least one of T-wave amplitude, P-wave amplitude, P-wave area, T-wave area, T-wave left slope, T-wave right slope, P-wave left slope, P-wave right slope, T-wave duration, P-wave duration, PR-interval, QRS duration, QRS amplitude, QRS area, QRS energy, QRS peak-to-peak ratio, or QT-segment length.

The ejection-fraction predictive model can be personalized to the mammal.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other reference mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 16 depicts a table depicting various patient characteristics and comorbidities for the patients involved in the example study and assessment of an ejection-fraction prediction model.

Like references and indicators among the drawings indicate like elements.

DETAILED DESCRIPTION

This specification discloses systems, methods, devices, and other techniques for estimating the cardiac ejection fraction of a mammal based on an electrocardiogram (ECG) of the mammal. In some implementations, machine-learning models such as neural networks are configured to process predictive inputs that characterize ECG data and output an indication of the estimated ejection fraction of a mammal. The model may be trained to account for complex combinations of features that are not otherwise discernible to a human, but that have been determined (e.g., by an iterative training process) to correlate to particular ejection-fraction characteristics. Additional detail about these and other techniques is provided in the following description of FIGS. 1-12.

Figure 1:
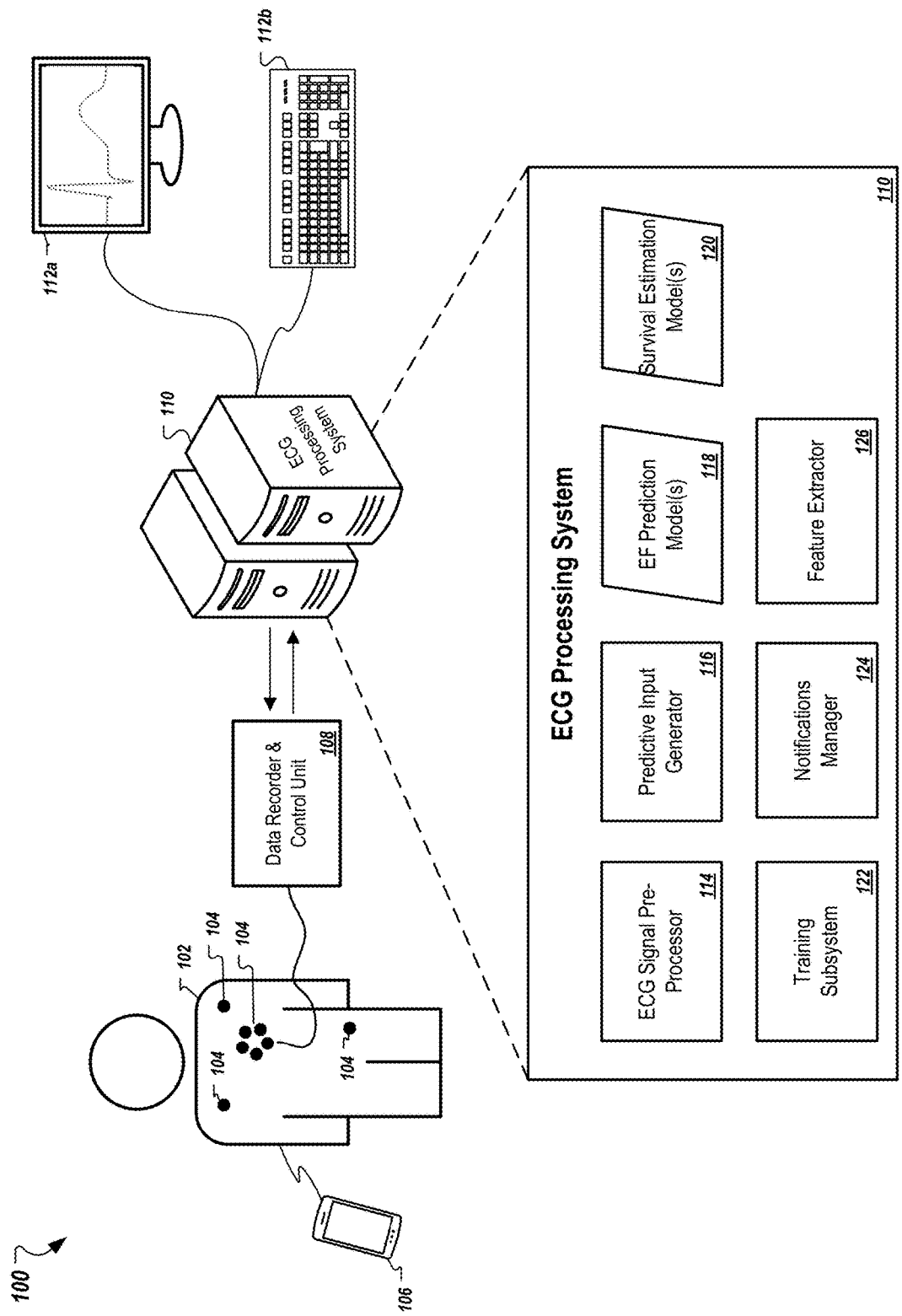
FIG. 1 is a conceptual diagram of an example system for recording and processing ECG data, and using the ECG data to estimate an ejection-fraction characteristic of a subject.

FIG. 1 is a conceptual diagram of an example system 100 for recording and processing ECG data, and using the ECG data to estimate an ejection-fraction characteristic of a subject 102. For the purpose of this example, the subject 102 will be considered as a human, and more specifically as a patient of a healthcare provider. However, it should be understood that the description is not limited to this example. In other implementations, the subject 102 may be a human who is not specifically associated with a healthcare provider, or may be any other mammal for which an appropriate model has been constructed to map ECG data to estimates of ejection fraction for the mammal.

A set of electrodes 104 are disposed on a surface of the patient 102 to enable recording of signals indicating the cardiac electrical activity of the patient 102 during an ECG procedure. In some implementations, 10 leads may be affixed to a patient to perform a standard 12-lead ECG recording (e.g., with several electrodes located on the chest near the region of the heart and other electrodes located on the limbs of the patient). The 12-lead ECG is beneficial to obtain multiple channels of ECG data, where the data for each channel represents a respective lead. Each lead is formed by the electrical potential between a pair of electrodes. Due to variances in electrode positioning, each lead provides a different view of the patient's cardiac electrical activity as a result of the different angles formed by the different pairs of electrodes for the different leads. For example, the signal from each lead can be recorded simultaneously for a period of time (e.g., 5, 10, or 15 seconds) to capture information about the timing and location of electrical activity along different radial directions.

In some implementations, ECG data can be recorded using a sensor platform or electrode configuration other than, or in addition to, the 12-lead ECG configuration. For example, a removable ECG patch may be affixed to the surface of a patient, where the patch includes two or more electrodes forming one, two, or more leads from which an ECG can be recorded. In some implementations, the patient 102 can manually contact a fixed pair of external electrodes with his or her fingers, or the patient 102 may wear a watch, wristband, chest band, or other device that secures two or more electrodes in position on the patient 102 to sense the patient's cardiac electrical activity. A mobile computing device (e.g., smartphone 106) may be used by the patient 102 or a healthcare provider to configure aspects of the ECG procedure in a clinical or non-clinical setting.

The system 100 further includes a data recorder and control unit 108, an ECG processing system 110, and one or more input/output devices 112a-b. In some implementations, wires that extend from each of the electrodes 104 are coupled to the data recorder and control unit 108 to permit recording of the electrical signals sensed by the electrodes. The unit 108, for example, may include an analog-to-digital (A/D) converter and other analog or digital signal conditioning circuits such amplifiers, filters, and the like.

The data recorder and controller unit 108 is communicably coupled to the ECG processing system 110. The ECG processing system 110 is a system of one or more computers, which may be distributed in one or more physical locations. System 110 may or may not be in the same physical location as the patient 102 and the data recorder and control unit 108. The system 110 may be coupled to peripheral devices such as a display screen 112a for presenting information to a user, and a mouse and keyboard 112 for receiving user inputs. Moreover, the system 110 may include a variety of components 114-126 that facilitate processing of ECG data to determine estimated ejection fraction characteristics, estimated survival rates, and for presenting information about such estimates.

For example, the system 110 can include a pre-processor 114 that digitally conditions ECG signals received from the data recorder and control unit 108. The pre-processor 114 may perform noise reduction, anti-aliasing, or other digital techniques to prepare ECG data describing the ECG of the patient 102 for further processing.

The system 110 further includes one or more ejection-fraction prediction models 118. These models 118 are generally configured to process one or more predictive inputs that characterize a patient's ECG data and, based on the predictive inputs, generate an estimated ejection-fraction characteristic for the patient 102. The ejection-fraction characteristic may indicate, for example, an absolute estimate of the patient's ejection-fraction (e.g., a particular value such as 50-percent, 45-percent, 40-percent, 35-percent, 30-percent, or another value) or a classification of the patient's estimated ejection-fraction (e.g., normal ejection-fraction greater than 50-percent, low ejection fraction between 35 and 50 percent, or very low ejection-fraction below 35-percent).

As described in further detail below, the ejection-fraction prediction model(s) 118 may be regression models, machine-learning models, or both. In some implementations, the model(s) 118 are feedforward, recurrent, or convolutional neural networks, or a capsule network. Neural network models may have fully connected layers and may employ an auto-encoder network. In some implementations, the system 110 stores and maintains multiple ejection-fraction prediction models 118. Each model 118 may correspond to a different set of patient characteristics (e.g., age, weight, gender, or other characteristics). When the ejection fraction for a new patient 102 is to be evaluated, the system 110 may select an appropriate one of the models 118 that correspond to characteristics matching those of the patient's 102. Each model 118 may be trained, for example, specifically on data points from patient(s) that have the corresponding characteristics for the model 118. Other types of machine-learning or regression models may also be applied such as support vector machines (SVMs), hidden Markov models (HMMs), and other linear and non-linear systems.

In some implementations, the system 110 maintains one or more survival estimation model(s) 120. The survival estimation model(s) 120 are configured to process ECG data, estimated ejection-fraction characteristics, or both, to generate a prognosis of the patient's estimated future survival rate (e.g., a 1, 2, 5, and/or 10-year survival rate) indicating a likelihood of surviving a cardiac condition based on the patient's ejection-fraction characteristic. For example, an ejection-fraction characteristic model 118 may be used to generate an estimated ejection-fraction characteristic for the patient. The survival estimation model(s) 120 may then map the estimated ejection-fraction characteristic to a future survival rate for the patient as determined from empirical data. For instance, a patient with a very low ejection fraction may have a lower estimated 5-year survival rate than a patient with normal ejection fraction. In other implementations, the survival estimation model(s) 120 may process predictive inputs that characterize a patient's ECG and derive an estimated survival rate for the patient 102 directly from the predictive inputs without first starting from the patient's estimated ejection fraction. In this way, characteristics of the patient's ECG other than or in addition to ejection fraction may be considered in determining an estimated survival rate for the patient 102. The survival estimation model(s) 120 may be regression models, machine-learning models, or both. In some implementations, the model(s) 120 are feedforward, recurrent, or convolutional neural networks, or a capsule network. Neural network models may have fully connected layers and may employ an auto-encoder network. In some implementations, the system 110 stores and maintains multiple survival estimation models 120. Each model 120 may correspond to a different set of patient characteristics (e.g., age, weight, gender, or other characteristics). When the ejection fraction for a new patient 102 is to be evaluated, the system 110 may select an appropriate one of the models 120 that correspond to characteristics matching those of the patient's 102. Each model 120 may be trained, for example, specifically on data points from patient(s) that have the corresponding characteristics for the model 120.

A predictive input generator 116 processes ECG data from the data recorder and control unit 108 or ECG signal pre-processor 114 to generate predictive inputs that are suitable for processing by the ejection-fraction prediction model(s) 118 or survival estimation model(s) 120. For example, the predictive input generator 116 may normalize and vectorize ECG data from one or more channels (corresponding to one or more leads) into a format expected by the ejection-fraction prediction model(s) 118. In some implementations, a predictive input contains a time-series of values indicating the amplitude of the ECG for one or more leads at each point in time at a specified sampling frequency over a period of time that spans one or more cardiac cycles (e.g., 1, 2, 5, or 10 seconds). In some examples, a predictive input can represent an ECG signal that spans a relatively short amount of time (e.g., 1, 2, 5, or 10 seconds), although in other examples the predictive input can represent an ECG signal for a relatively longer time (e.g., 30 seconds, 1 minute, 2 minutes, 5 minutes, 10 minutes or longer). In some implementations, the predictive input generator 116 averages the ECG from two or more cardiac cycles to generate an averaged ECG that represents an averaged cardiac cycle of the patient 102. In some implementations, the predictive input generator 116 selects a portion of the ECG corresponding to a single cardiac cycle and characterizes only the selected portion of the ECG in the predictive input. The selected portion is thus a representative cardiac cycle of the patient 102.

In some implementations, rather than processing actual time-series data representing the amplitude of an ECG waveform over time, the ejection-fraction predictive model(s) 118 and survival estimation model(s) 120 may instead process predictive inputs that indicate values of one or more morphological features of the patient's ECG. Morphological features are parameters that characterize the shape of an ECG waveform or a portion of the ECG waveform such as the P-wave, QRS-complex, or T-wave. Example morphological features that may be identified in a predictive input include T-wave amplitude, P-wave amplitude, P-wave area, T-wave area, T-wave left slope, T-wave right slope, P-wave left slope, P-wave right slope, T-wave duration, P-wave duration, PR-interval, QRS duration, QRS amplitude, QRS area, QRS energy, QRS peak-to-peak ratio, QT-segment length, or a combination of two or more of these. A number of these features are graphically illustrated on the example ECG waveform 300 in FIG. 3. In some implementations, the system 110 includes a feature extractor 126 that analyzes ECG data and determines values of any applicable morphological features to include the predictive input that will be processed by an ejection-fraction prediction model 118.

The system 110 further includes a training subsystem 122 and a notifications manager 124. The training subsystem 122 is configured to train the ejection-fraction prediction model(s) 118, the survival estimation model(s) 120, or both. An example process 600 performed by the training subsystem 122 to train an ejection-fraction prediction model 118 is described with respect to FIG. 6. The notifications manager 124 is configured to provide an estimated ejection-fraction characteristic, estimated survival rate, or both, for output to one or more users. In some implementations, the notifications manager 124 provides an estimated ejection fraction characteristic for display on screen 112a. Additionally, one or more notification services may register with the computing system 110 so that the notifications manager 124 pushes the results of an estimated ejection-fraction characteristic, survival rate estimation, or both to each of the registered services for presentation by one or more means (e.g., on a smartphone, at a healthcare provider's clinic, for visual, audible, and/or haptic presentation).

Figure 2:
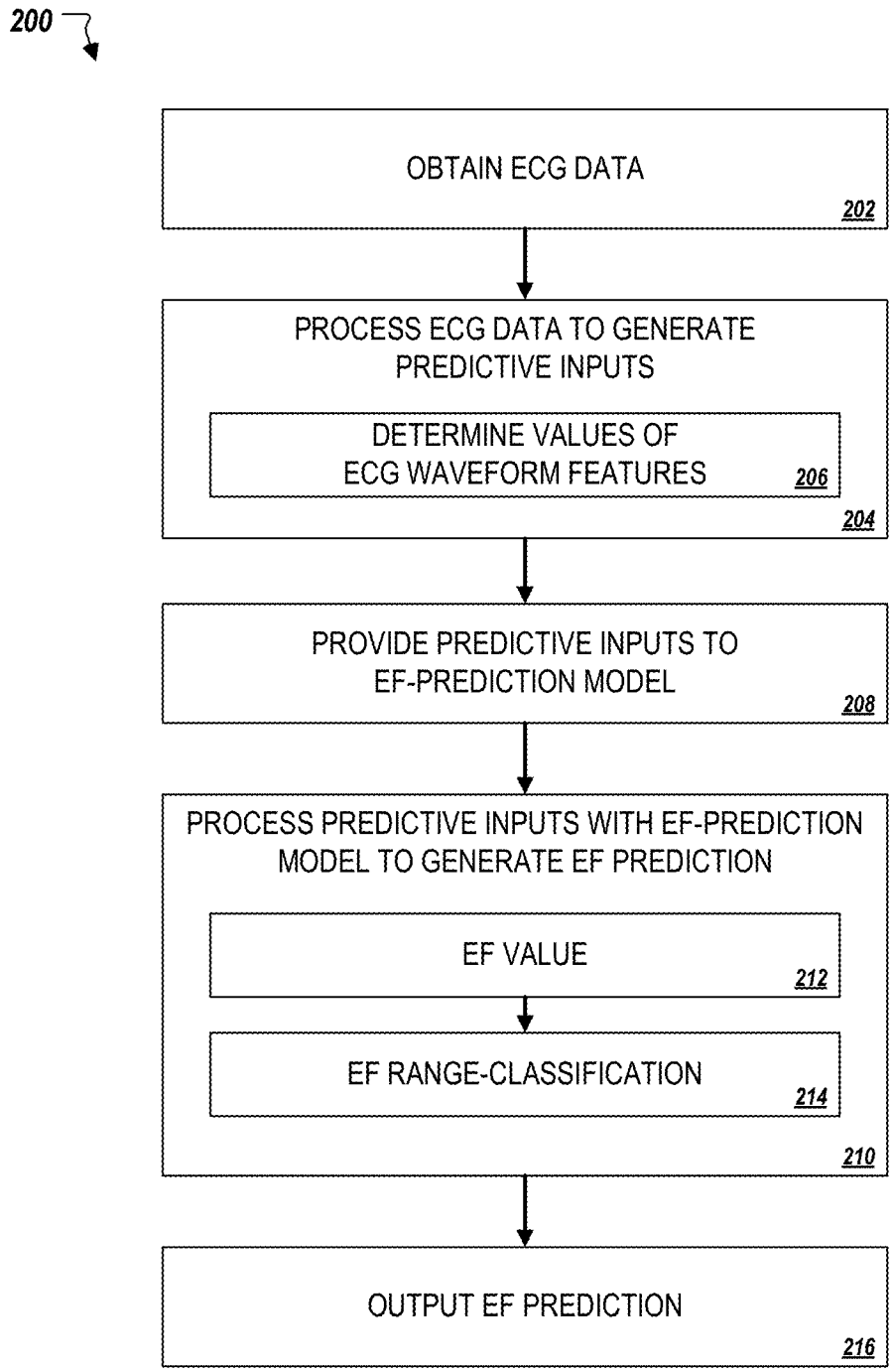
FIG. 2 is a flowchart of an example process for estimating an ejection-fraction characteristic of a subject using ECG data.

FIG. 2 is a flowchart of an example process 200 for estimating an ejection-fraction characteristic of a subject using ECG data. The process 200 can be performed by a computing system, e.g., system 110 of FIG. 1. At stage 202, the system obtains ECG data for a patient. The ECG data may include one or more channels that each represents the ECG signal for a respective lead of an ECG procedure, and data from each channel may be temporally aligned. The ECG data may span a single cardiac cycle of the patient, a portion of a cardiac cycle, or multiple cardiac cycles. At stage 204, a predictive input generator of the system generates one or more predictive inputs from the ECG data to feed to an ejection-fraction prediction model, e.g., ejection-fraction prediction model 118. In some implementations, the predictive inputs represent a time-series of values for the ECG waveform. In other implementations, the predictive inputs represent values of morphological features of the ECG waveform (stage 206). At stage 208, the system provides the predictive inputs to the ejection-fraction prediction model for processing. At stage 210, the ejection-fraction prediction model processes the predictive inputs that represent the patient's ECG result to generate an estimated (predicted) ejection-fraction characteristic. In some implementations (212), the ejection-fraction characteristic is an absolute estimate of the patient's ejection fraction that identifies a specific value for the ejection fraction. In other implementations (214), the ejection-fraction characteristic is a category or range of ejection-fraction values (e.g., very low ejection fraction, low ejection fraction, or normal ejection fraction). For example, the ejection-fraction model may be trained to classify a patient's ejection fraction into one of two, three, or more possible ejection-fraction categories defined by specified threshold ejection-fraction values. A binary classification model may classify a patient's ejection fraction into two possible categories. The system then stores and/or outputs the estimated ejection-fraction characteristic at stage 216, e.g., for presentation to the patient or his or her healthcare provider.

In some implementations, the ejection-fraction prediction model may be trained and configured to estimate not the patient's current ejection-fraction characteristic (as is described in other implementations), but instead to predict a patient's risk of developing a low or very low ejection fraction at a future time (e.g., over the next 1 month, 6 months, 1 year, 2 years, 5 years, or more) by detecting subtle features or changes in the patient's ECG that indicate early manifestations of the disease.

Figure 3:
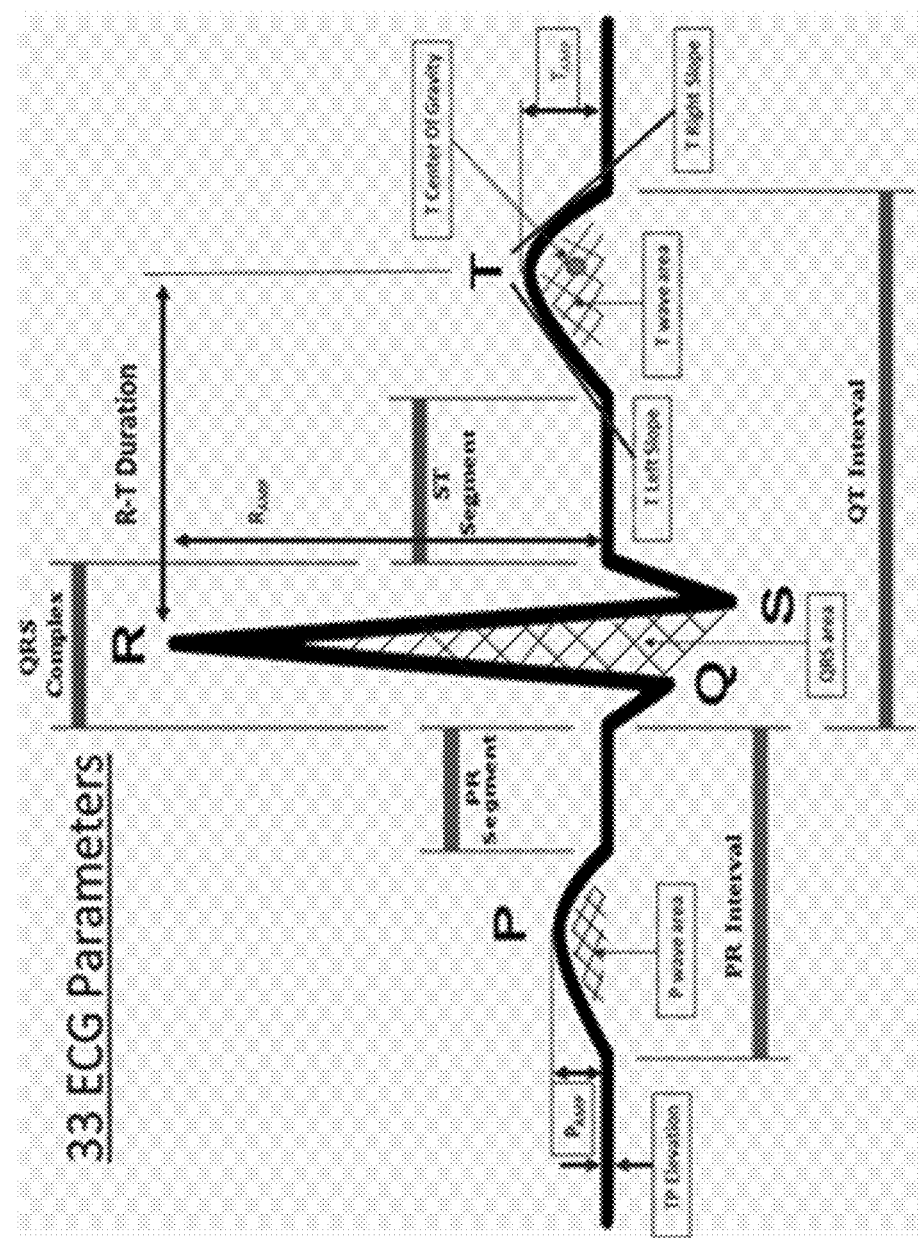
FIG. 3 is a diagram of an example ECG tracing for one heartbeat of a patient. The ECG tracing shows constituent segments of the beat and various morphological waveform features.

FIG. 3 is a diagram of an example ECG tracing 300 for one heartbeat of a patient. The ECG tracing shows constituent segments of the beat and various morphological waveform features.

Figure 4:
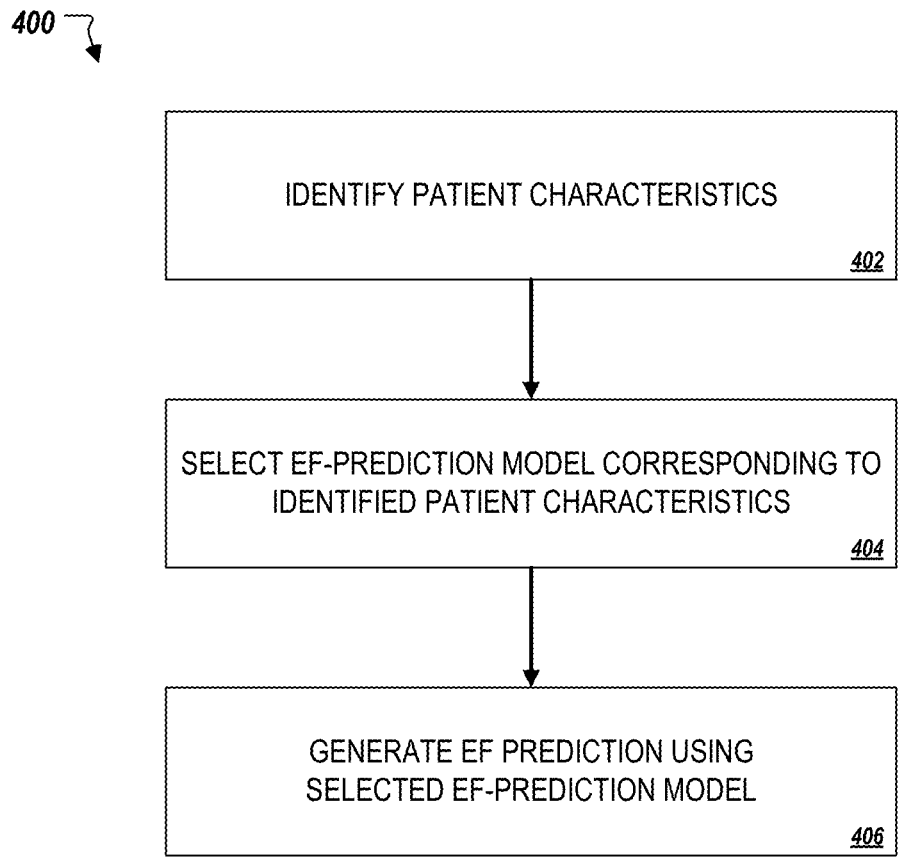
FIG. 4 is a flowchart of an example process for selecting and using an appropriate ejection-fraction prediction model that corresponds to specified characteristics of a subject.

FIG. 4 is a flowchart of an example process 400 for selecting and using an appropriate ejection-fraction prediction model that corresponds to the characteristics of a patient. The process 400 can be performed by a computing system, such as system 110 of FIG. 1. In some instances, a global ejection-fraction prediction model can be trained and used for a wide range of patients. However, in other instances, more accurate or reliable estimates of a patient's ejection fraction may be determined using a personalized model that is specific to the patient, or using a semi-personalized model that has been trained on ECG data and measured ejection-fraction characteristics from a population of patients having identical or similar characteristics as a new patient for whom an ejection fraction estimate is desired. For example, multiple ejection-fraction prediction models may be generated that each correspond to a different set of patient characteristics such as age, height, weight, body-mass index (BMI), gender, family history, any indication of other co-morbidities such as diabetes, hypertension, hyperlipidemia, high sensitivity C reactive protein (CRP), tobacco use, history of coronary artery diseases, history of inflammatory diseases, or a combination of these. At stage 402, the system identifies a set of characteristics for the patient for whom an estimated ejection fraction characteristic is to be determined. At stage 404, the system selects one of the ejection-fraction prediction models that corresponds to the identified set of characteristics for the patients. For example, for a male patient over the age 50, a model that was trained on data from subjects having similar characteristics as the patient may be selected rather than other models that were trained on data from subjects having other characteristics. At stage 406, the system generates an ejection-fraction prediction using the selected ejection-fraction prediction model that corresponds to the patient's characteristics. For example, the system may generate an estimated ejection-fraction characteristic with the selected model according to the process 200 described with respect to FIG. 2.

Figure 5:
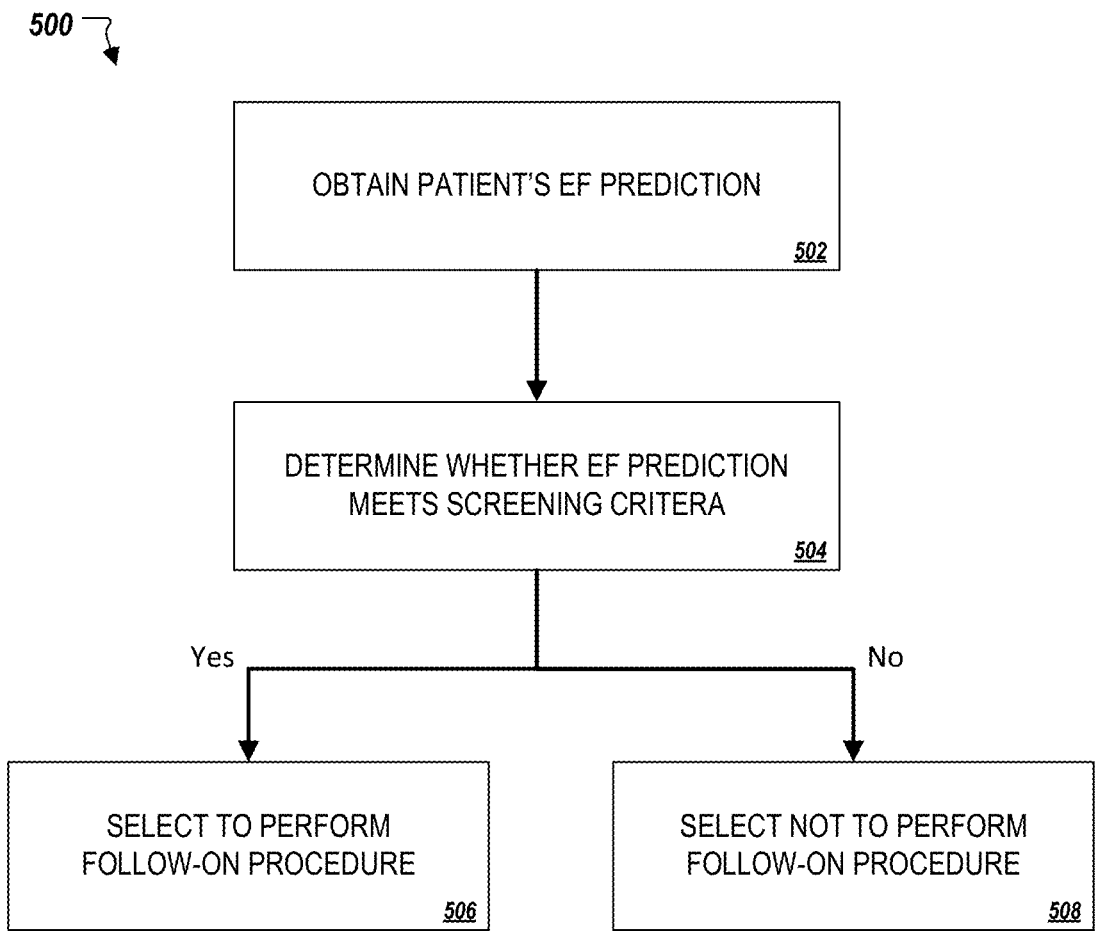
FIG. 5 is a flowchart of an example process for using an ECG-based ejection-fraction estimate as a screening tool to determine whether further evaluation is warranted.

Although ECG-based estimates of a patient's ejection fraction can be useful screening procedure, further evaluation of a patient may be warranted based on the results of an ECG-based screening procedure. FIG. 5 is a flowchart of an example process 500 for using an ECG-based approach to screen for potentially problematic ejection-fraction levels. The process 500 may be automated, e.g., performed by computing system 110, or may be performed by healthcare provider or other appropriate individual. At stage 502, a patient's estimated ejection-fraction characteristic is obtained, e.g., based on the process 200 described with respect to FIG. 2. At stage 504, the system determines whether the estimated ejection-fraction characteristic, and optionally additional factors, meet one or more screening criteria that are to guide a decision whether to further evaluation of the patient's condition is warranted. For example, the estimated ejection-fraction characteristic may be an absolute value that indicates the predicted ejection fraction of a patient and the screening criteria may include a threshold ejection fraction (e.g., 35-percent or 50-percent). If the estimated ejection fraction of the patient is below the threshold, a follow-on procedure for further evaluation can be performed on the patient. The follow-on procedure may be, for example, an echocardiogram, an MRI, a CT scan, a nuclear medicine diagnostic, or a combination of these. In some implementations, if the patient's ejection-fraction characteristic is a classification into a range of ECG values that is deemed risky or unsafe, further medical evaluation can be performed on the patient.

In some implementations, if the patient's ejection-fraction is below the threshold (e.g., 35-percent or 50-percent), or the patient's ejection-fraction characteristic is a classification into a range of ECG values that is deemed risky or unsafe, therapeutic medicine can be administered to the patient, or treatment can be performed on the patient. Such medicine or treatment may include beta blockers, angiotensin receptor antagonists, statins (in coronary artery disease), implantable defibrillators, cardiac resynchronization devices and other well defined treatments (see 2013 ACCF/AHA Guideline for the Management of Heart Failure. *Circulation*. 2013; 128:

e240-e327; and 2016 ACC/AHA/HFSA Focused Update on New Pharmacological Therapy for Heart Failure, *Circulation.* 2016; 134:e282-e293). In some implementations, if the patient's ejection-fraction is below the threshold (e.g., 35-percent or 50-percent), or the patient's ejection-fraction characteristic is a classification into a range of ECG values that is deemed risky or unsafe, additional diagnostic testing with therapeutic interventions include screening for inflammatory and other systemic conditions that also have specific therapies or coronary angiography or other imaging to find coronary artery disease, which in turn has well defined treatments.

Figure 6:
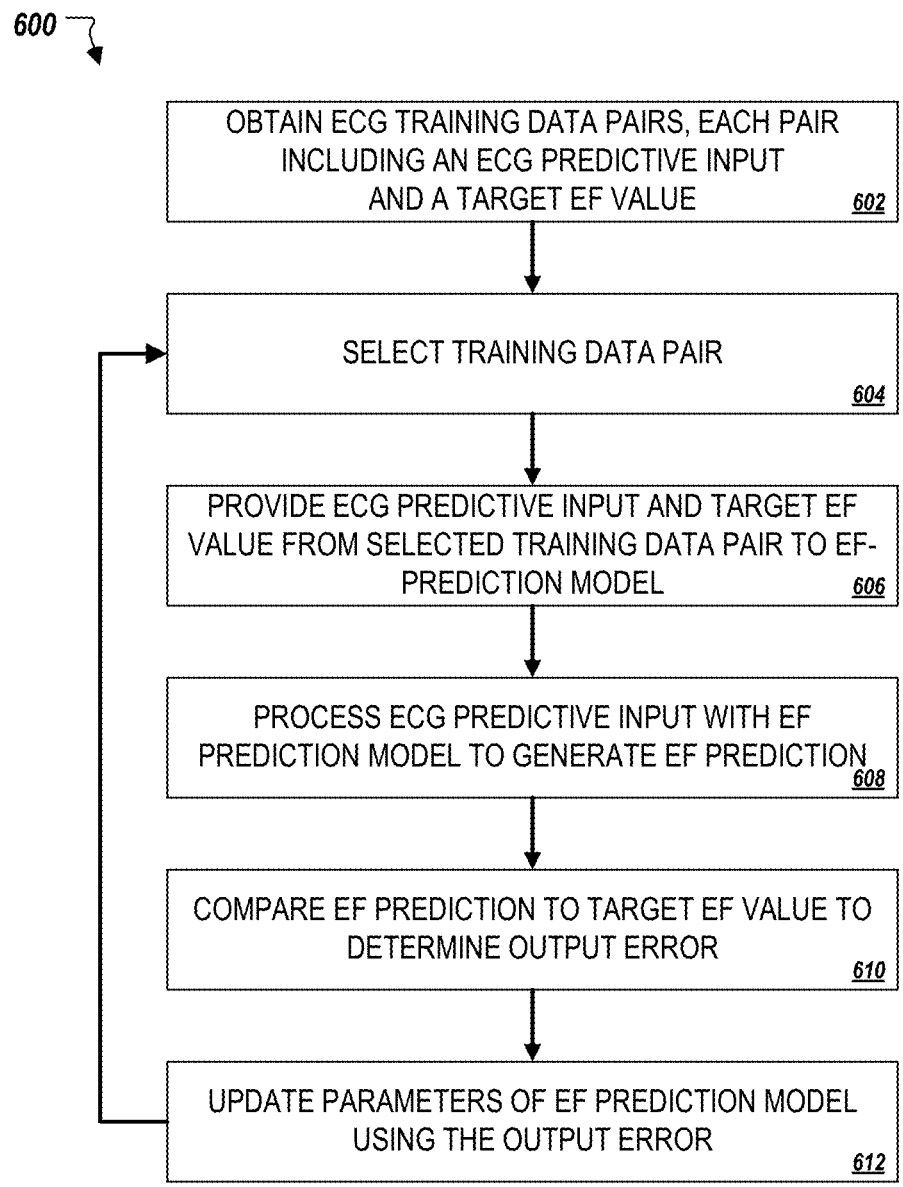
FIG. 6 is a flowchart of an example process for training an ejection-fraction prediction model, such as a neural network-based model.

FIG. 6 is a flowchart of an example process 600 for training an ejection-fraction prediction model, such as a neural network-based model. In some implementations, machine-learning techniques such as gradient descent, including batch gradient descent or stochastic gradient descent, may be used to train the ejection-fraction model. The process 600 may be performed by a computing system such as the training subsystem 122 described with respect to FIG. 1. At stage 602, the system obtains a set of multiple training data pairs. Each pair includes an ECG predictive input that characterizes a particular patient's ECG and a target ejection-fraction characteristic for the patient. The target ejection-fraction characteristic may be a "true" or measured ejection-fraction characteristic determined by an echocardiogram or other available procedure. In some cases, the model is trained on data from many different patients. If the model is semi-personalized, the patients represented in the training set may share a set of common characteristics with each other. At stage 604, the training system selects a first training data pair for processing. At stage 606, the predictive input from the training data pair is provided to the ejection-fraction prediction model. The ejection-fraction prediction model may be, for example, a neural network machine-learning model having one or more layers of perceptrons having associated weights/parameters for activation functions associated with each perceptron. These weights may be randomly initialized when training starts, and gradually refined over time as additional training iterations are performed. At stage 608, the system processes the predictive input according to the current weights/parameters of the model and generates an estimated ejection-fraction characteristic. At stage 610, the estimated ejection-fraction characteristic is compared to the target ejection-fraction characteristic to determine an output error. This output error is then back-propagated through the network using gradient descent to update the current weights/parameters of the neural network. The process then returns to stage 604 where another training data pair is selected, and the operations are 604-612 are repeated until a training termination condition occurs.

Although the ejection-fraction prediction model may be trained on a large dataset, the model itself may be relatively compact. After training, the model may be relatively compact and can predict ejection-fraction characteristics with less computational demand than may have been required during training.

While the process 600 generally pertains to a supervised learning process, in some implementations the ejection-fraction prediction model may be trained using unsupervised learning techniques.

Figure 7:
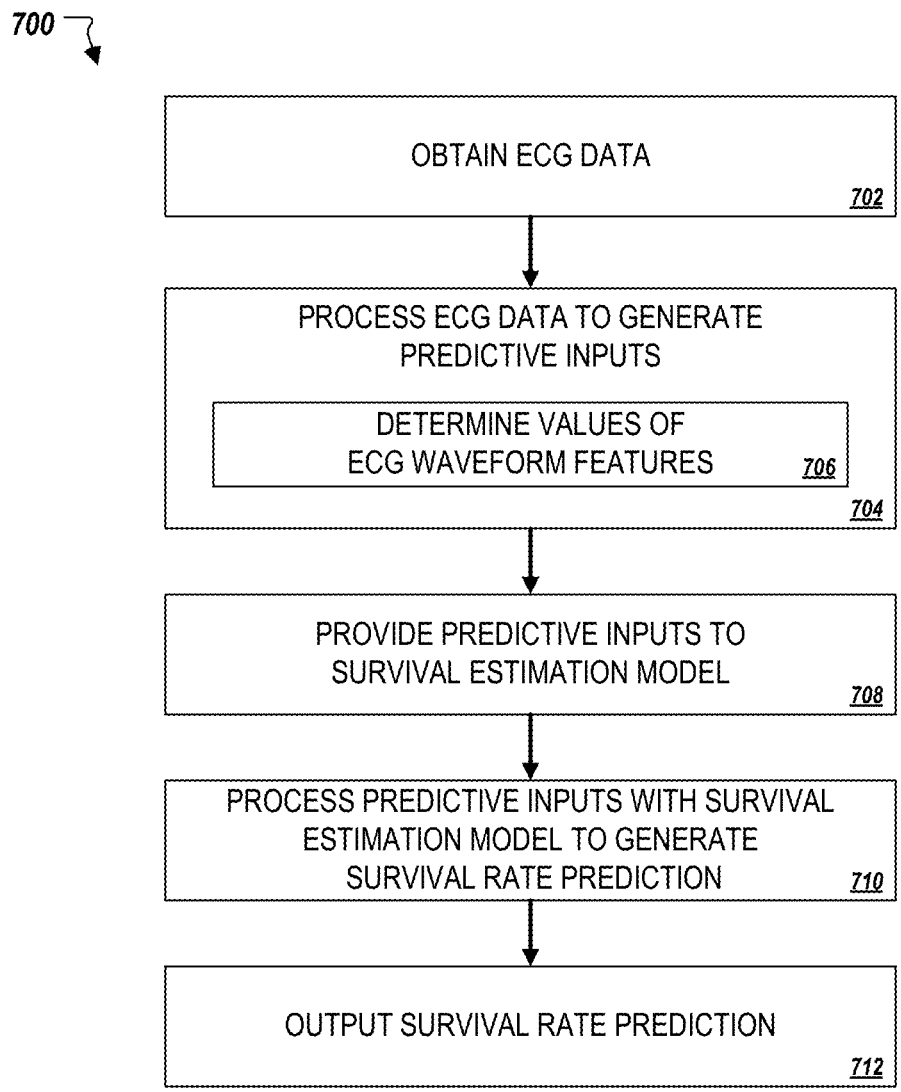
FIG. 7 is a flowchart of an example process for predicting a subject's survival rate from cardiac conditions, such as low or very low ejection fraction, from ECG data for the subject.

FIG. 7 is a flowchart of an example process 700 for predicting a subject's survival rate from cardiac conditions, such as low or very low ejection fraction, from ECG data for the subject. In some implementations, the process 700 is performed by a computing system that includes a survival estimation model such as model 120 of ECG processing system 110 (FIG. 1). At stage 702, the system obtains ECG data for a patient. The ECG data may include one or more channels that each represent the ECG signal for a respective lead of an ECG procedure, and data from each channel may be temporally aligned. The ECG data may span a single cardiac cycle of the patient, a portion of a cardiac cycle, or multiple cardiac cycles. At stage 704, a predictive input generator of the system generates one or more predictive inputs from the ECG data to feed to the survival estimation model. In some implementations, the predictive inputs represent a time-series of values for the ECG waveform. In other implementations, the predictive inputs represent values of morphological features of the ECG waveform (706). At stage 708, the predictive inputs are provided to the survival estimation model, and at stage 710 the model processes the predictive inputs to determine an estimated survival rate of the patient based on the patient's ECG. The estimated survival rate may be, for example, a 1-month, 1-year, 2-year, 3-year, 4-year, 5-year, or 10-year prognosis. The system can then provide the survival rate estimation for output, including for presentation to the patient, his or her healthcare provider, or both (stage 712).

Figure 8:
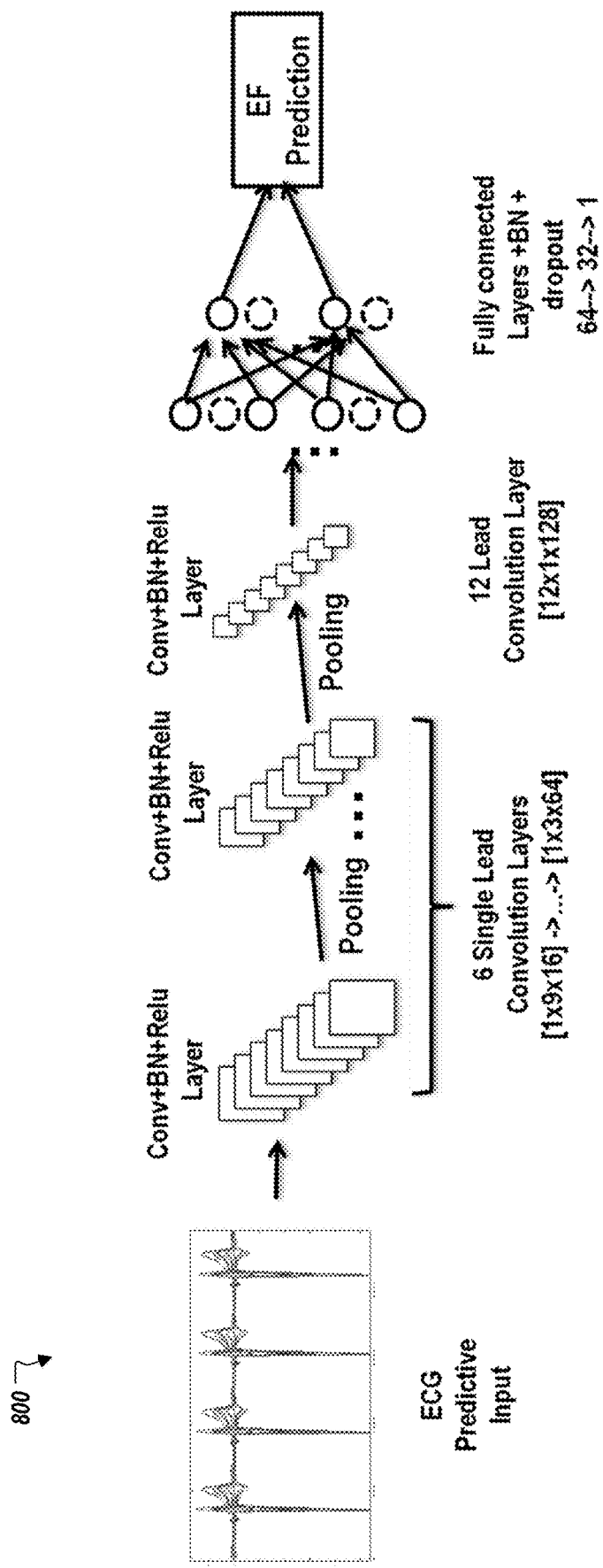
FIG. 8 is a diagram of an example neural network model for estimating an ejection-fraction characteristic of a subject from ECG data.

FIG. 8 is a diagram of an example neural network model 800 for estimating an ejection-fraction characteristic of a subject from ECG data. The model 800 processes an ECG predictive input characterizing one or more channels of the patient's ECG. As can be seen in FIG. 8, the model 800 can include an input layer of perceptrons and/or sigmoid neurons, an output layer, and one or more hidden layers therebetween. For example, the data from multiple channels may be processed and pooled until the data is provided to a fully-connected layer of the network. The model 800 may output an estimated value or classification of an ejection-fraction characteristic for the patient.

In some implementations, the neural network model 800 includes multiple convolutional layers for feature extract. Each convolutional layer can include a constant or variable-length filter that focuses attention on the current lead or multiple leads of the ECG at the same time (e.g., k×1 or k×m leads). Following the convolutional layer, the network can include one or more fully connected layers with the same or different number of neurons in each. None, one, or more recurrent neural network layers can be added before, after, or in parallel to the convolutional layers for temporal feature extraction. Skip layers and neurons may or may not be included.

Figure 9:
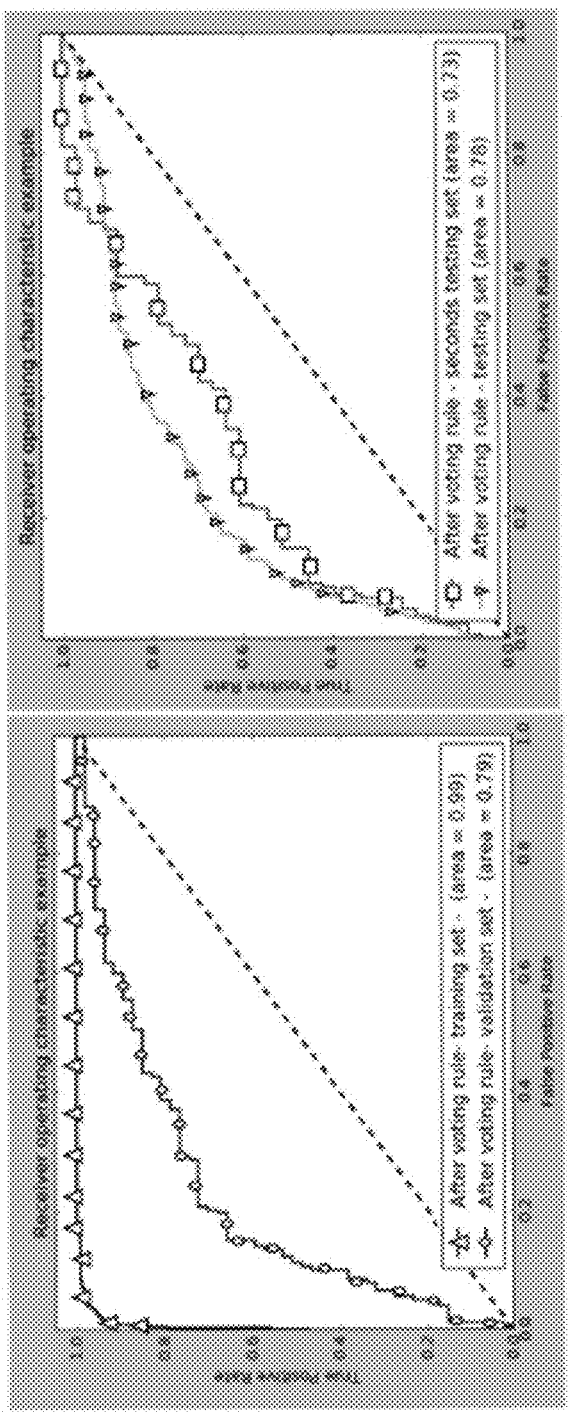
FIG. 9 shows results of a first neural-network implementation of an ejection-fraction prediction model that classifies patients into groups according to whether the patients are predicted to have ejection-fraction above or below 50-percent.

FIG. 9 shows results 900 of a first neural-network implementation of an ejection-fraction prediction model that classifies patients into groups according to whether the patients are predicted to have ejection-fraction above or below 50-percent.

Figure 10:
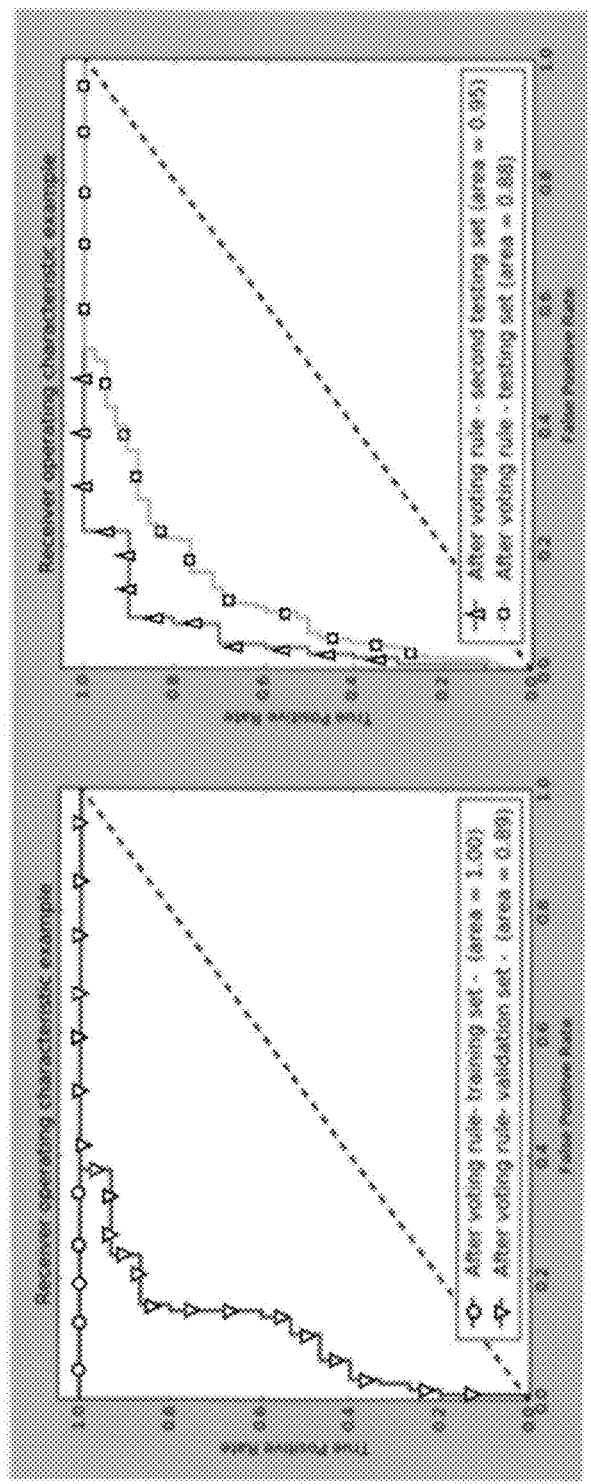
FIG. 10 shows results of a second neural-network implementation of an ejection-fraction prediction model that classifies patients into groups according to whether the patients are predicted to have ejection-fraction above or below 35-percent.

FIG. 10 shows results 1000 of a second neural-network implementation of an ejection-fraction prediction model that classifies patients into groups according to whether the patients are predicted to have ejection-fraction above or below 35-percent.

Figure 11:
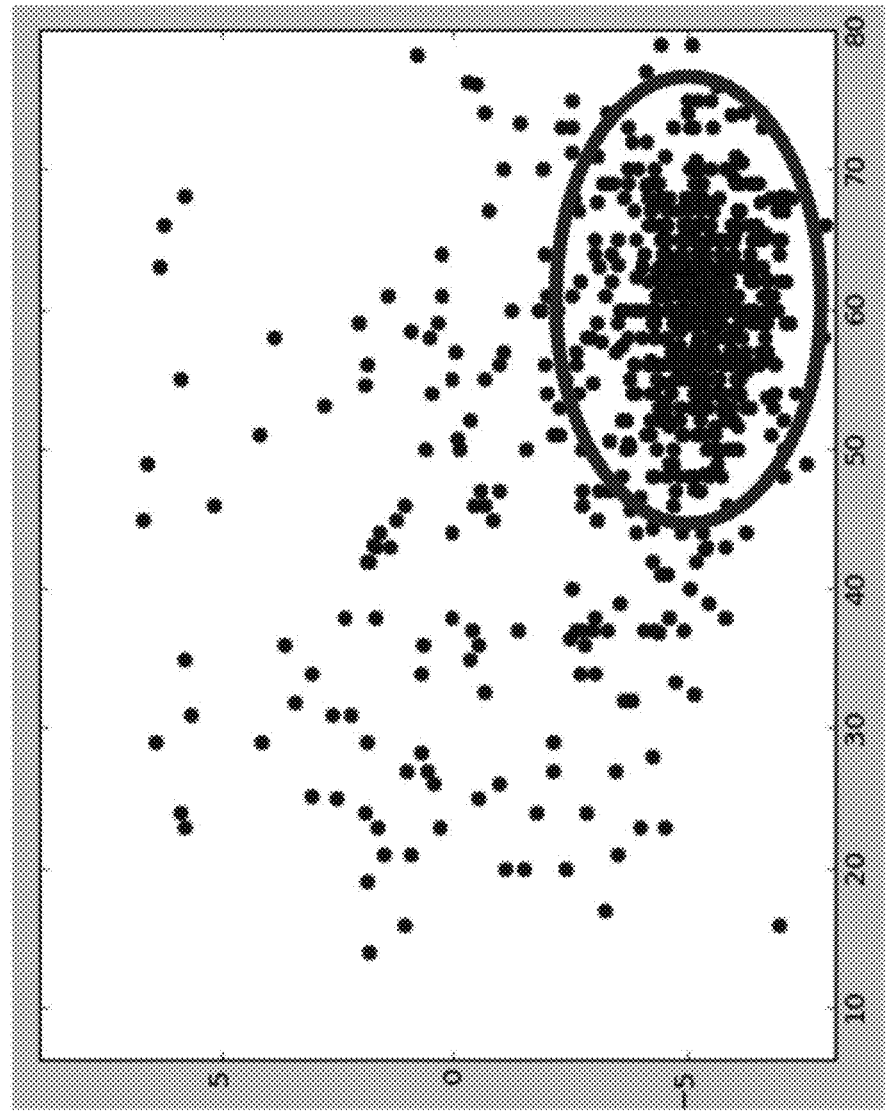
FIG. 11 is a plot showing correlation between model output and true ejection-fraction numerical values in study.

FIG. 11 is a plot 1100 showing correlation between model output and true ejection-fraction numerical values in study.

Although a number of examples are described herein for detecting dysfunctional (low) ejection-fraction in a patient using data from a standard 12-lead ECG, in other implementations fewer leads—including even a single-lead—ECG, can be used to effectively detect instances of low ejection fraction or to identify individuals who are susceptible to an increased risk of developing ejection fraction within a future period of time (e.g., 5 years). An ejection-fraction prediction model can be trained and implemented based on data from any number of ECG leads, including a single lead, any multi lead configuration and a standard 12-lead ECG. For example, a single lead ECG based on Lead 1 has shown to be particularly effective at providing reliable data from which an ejection-fraction prediction model can generate an ejection-fraction prediction. Ejection fraction prediction based on single lead ECG, or other non-traditional electrodes (e.g., less than standard 12-lead ECG), can advantageously expand access to screening devices that implement the ejection fraction prediction model described herein. For example, a pair of electrodes may be integrated with or communicatively coupled to a smartphone or other portable electronic device allowing an individual to conveniently capture his or her ECG and rapidly obtain a prediction result, e.g., by contacting the electrodes with his or her fingertips. In other implementations, the electrodes may be provided in a wearable patch for continuous monitoring over a period of time.

Yet another advantage that can be achieved, in certain instances, by at least some of the implementations described herein is the ability to detect low ejection fraction based on a short, single time profile of ECG data for a patient (e.g., from a single lead or multiple leads). For example, the system may only require to process a relatively short sample of ECG data to generate a high-confidence prediction of a patient's ejection-fraction condition, such as whether the patient has low EF. In some implementations, the ejection fraction prediction model is configured to predict whether a patient has low EF (e.g., less than 35, 40, or 50-percent EF) based on a 60-second ECG sample or less. In some implementations, the ejection fraction prediction model is configured to predict whether a patient has low EF (e.g., less than 35, 40, or 50-percent EF) based on a 30-second ECG sample or less. In some implementations, the ejection fraction prediction model is configured to predict whether a patient has low EF (e.g., less than 35, 40, or 50-percent EF) based on a 20-second ECG sample or less. In some implementations, the ejection fraction prediction model is configured to predict whether a patient has low EF (e.g., less than 35, 40, or 50-percent EF) based on a 15-second ECG sample or less. In some implementations, the ejection fraction prediction model is configured to predict whether a patient has low EF (e.g., less than 35, 40, or 50-percent EF) based on a 10-second ECG sample or less. In some implementations, the ejection fraction prediction model is configured to predict whether a patient has low EF (e.g., less than 35, 40, or 50-percent EF) based on a 5-second ECG sample or less. In some implementations, the ejection fraction prediction model is configured to predict whether a patient has low EF (e.g., less than 35, 40, or 50-percent EF) based on a 2-second ECG sample or less. The acquisition time for the ECG can thus be relatively short and convenient for the patient. Additionally, the use of a machine-learning model such as a convolutional neural network that has been trained on a large dataset can permit fast processing enables a computing system executing the model to return an ejection fraction prediction result based on the ECG input in a relatively short amount of time.

Particular implementations have been described with respect to models that estimate or predict an individual's ejection fraction. However, it should be appreciated that these techniques can be extended more generally to models that facilitate detection of a variety of present or impending structural heart diseases, including abnormal ejection fraction, left ventricular mass abnormality (e.g., elevated left ventricular mass, low left ventricular mass), valvular heart disease, ischemic heart disease, appendage abnormalities, presence of shunts or patent foramen ovale (PFO), heart chamber enlargement (e.g., left atrial, right atrial, left ventricular, right ventricular), or a combination of these and/or other structural heart diseases.

Figure 12:
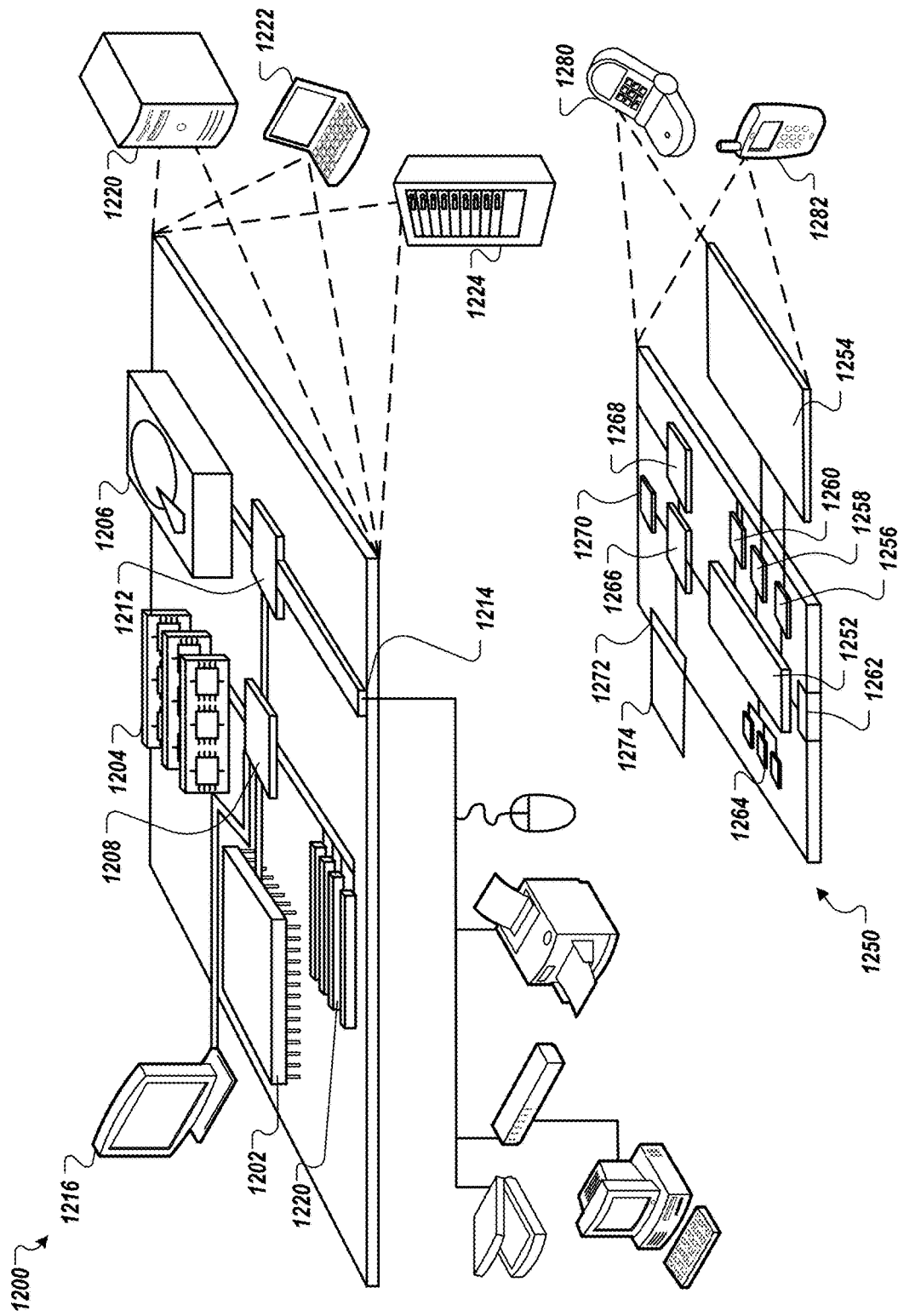
FIG. 12 is a block diagram of example computing devices that may be used to implement the systems, methods, devices, and other techniques described in this specification.

FIG. 12 is a block diagram of computing devices 1200, 1250 that may be used to implement the systems and methods described in this document, as either a client or as a server or plurality of servers. Computing device 1200 is intended to represent various forms of digital computers, such as laptops, desktops, workstations, personal digital assistants, servers, blade servers, mainframes, and other appropriate computers. Computing device 1250 is intended to represent various forms of mobile devices, such as personal digital assistants, cellular telephones, smartphones, and other similar computing devices. Additionally computing device 1200 or 1250 can include Universal Serial Bus (USB) flash drives. The USB flash drives may store operating systems and other applications. The USB flash drives can include input/output components, such as a wireless transmitter or USB connector that may be inserted into a USB port of another computing device. The components shown here, their connections and relationships, and their functions, are meant to be exemplary only, and are not meant to limit implementations described and/or claimed in this document.

Computing device 1200 includes a processor 1202, memory 1204, a storage device 1206, a high-speed interface 1208 connecting to memory 1204 and high-speed expansion ports 1210, and a low speed interface 1212 connecting to low speed bus 1214 and storage device 1206. Each of the components 1202, 1204, 1206, 1208, 1210, and 1212, are interconnected using various busses, and may be mounted on a common motherboard or in other manners as appropriate. The processor 1202 can process instructions for execution within the computing device 1200, including instructions stored in the memory 1204 or on the storage device 1206 to display graphical information for a GUI on an external input/output device, such as display 1216 coupled to high speed interface 1208. In other implementations, multiple processors and/or multiple buses may be used, as appropriate, along with multiple memories and types of memory. Also, multiple computing devices 1200 may be connected, with each device providing portions of the necessary operations (e.g., as a server bank, a group of blade servers, or a multi-processor system).

The memory 1204 stores information within the computing device 1200. In one implementation, the memory 1204 is a volatile memory unit or units. In another implementation, the memory 1204 is a non-volatile memory unit or units. The memory 1204 may also be another form of computer-readable medium, such as a magnetic or optical disk.

The storage device 1206 is capable of providing mass storage for the computing device 1200. In one implementation, the storage device 1206 may be or contain a computer-readable medium, such as a floppy disk device, a hard disk device, an optical disk device, or a tape device, a flash memory or other similar solid state memory device, or an array of devices, including devices in a storage area network or other configurations. A computer program product can be tangibly embodied in an information carrier. The computer program product may also contain instructions that, when executed, perform one or more methods, such as those described above. The information carrier is a computer- or machine-readable medium, such as the memory 1204, the storage device 1206, or memory on processor 1202.

The high speed controller 1208 manages bandwidth-intensive operations for the computing device 1200, while the low speed controller 1212 manages lower bandwidth-intensive operations. Such allocation of functions is exemplary only. In one implementation, the high-speed controller 1208 is coupled to memory 1204, display 1216 (e.g., through a graphics processor or accelerator), and to high-speed expansion ports 1210, which may accept various expansion cards (not shown). In the implementation, low-speed controller 1212 is coupled to storage device 1206 and low-speed expansion port 1214. The low-speed expansion port, which may include various communication ports (e.g., USB, Bluetooth, Ethernet, wireless Ethernet) may be coupled to one or more input/output devices, such as a keyboard, a pointing device, a scanner, or a networking device such as a switch or router, e.g., through a network adapter.

The computing device 1200 may be implemented in a number of different forms, as shown in the figure. For example, it may be implemented as a standard server 1220, or multiple times in a group of such servers. It may also be implemented as part of a rack server system 1224. In addition, it may be implemented in a personal computer such as a laptop computer 1222. Alternatively, components from computing device 1200 may be combined with other components in a mobile device (not shown), such as device 1250. Each of such devices may contain one or more of computing device 1200, 1250, and an entire system may be made up of multiple computing devices 1200, 1250 communicating with each other.

Computing device 1250 includes a processor 1252, memory 1264, an input/output device such as a display 1254, a communication interface 1266, and a transceiver 1268, among other components. The device 1250 may also be provided with a storage device, such as a microdrive or other device, to provide additional storage. Each of the components 1250, 1252, 1264, 1254, 1266, and 1268, are interconnected using various buses, and several of the components may be mounted on a common motherboard or in other manners as appropriate.

The processor 1252 can execute instructions within the computing device 1250, including instructions stored in the memory 1264. The processor may be implemented as a chipset of chips that include separate and multiple analog and digital processors. Additionally, the processor may be implemented using any of a number of architectures. For example, the processor 1252 may be a CISC (Complex Instruction Set Computers) processor, a RISC (Reduced Instruction Set Computer) processor, or a MISC (Minimal Instruction Set Computer) processor. The processor may provide, for example, for coordination of the other components of the device 1250, such as control of user interfaces, applications run by device 1250, and wireless communication by device 1250.

Processor 1252 may communicate with a user through control interface 1258 and display interface 1256 coupled to a display 1254. The display 1254 may be, for example, a TFT (Thin-Film-Transistor Liquid Crystal Display) display or an OLED (Organic Light Emitting Diode) display, or other appropriate display technology. The display interface 1256 may comprise appropriate circuitry for driving the display 1254 to present graphical and other information to a user. The control interface 1258 may receive commands from a user and convert them for submission to the processor 1252. In addition, an external interface 1262 may be provide in communication with processor 1252, so as to enable near area communication of device 1250 with other devices. External interface 1262 may provide, for example, for wired communication in some implementations, or for wireless communication in other implementations, and multiple interfaces may also be used.

The memory 1264 stores information within the computing device 1250. The memory 1264 can be implemented as one or more of a computer-readable medium or media, a volatile memory unit or units, or a non-volatile memory unit or units. Expansion memory 1274 may also be provided and connected to device 1250 through expansion interface 1272, which may include, for example, a SIMM (Single In Line Memory Module) card interface. Such expansion memory 1274 may provide extra storage space for device 1250, or may also store applications or other information for device 1250. Specifically, expansion memory 1274 may include instructions to carry out or supplement the processes described above, and may include secure information also. Thus, for example, expansion memory 1274 may be provide as a security module for device 1250, and may be programmed with instructions that permit secure use of device 1250. In addition, secure applications may be provided via the SIMM cards, along with additional information, such as placing identifying information on the SIMM card in a non-hackable manner.

The memory may include, for example, flash memory and/or NVRAM memory, as discussed below. In one implementation, a computer program product is tangibly embodied in an information carrier. The computer program product contains instructions that, when executed, perform one or more methods, such as those described above. The information carrier is a computer- or machine-readable medium, such as the memory 1264, expansion memory 1274, or memory on processor 1252 that may be received, for example, over transceiver 1268 or external interface 1262.

Device 1250 may communicate wirelessly through communication interface 1266, which may include digital signal processing circuitry where necessary. Communication interface 1266 may provide for communications under various modes or protocols, such as GSM voice calls, SMS, EMS, or MMS messaging, CDMA, TDMA, PDC, WCDMA, CDMA2000, or GPRS, among others. Such communication may occur, for example, through radio-frequency transceiver 1268. In addition, short-range communication may occur, such as using a Bluetooth, WiFi, or other such transceiver (not shown). In addition, GPS (Global Positioning System) receiver module 1270 may provide additional navigation- and location-related wireless data to device 1250, which may be used as appropriate by applications running on device 1250.

Device 1250 may also communicate audibly using audio codec 1260, which may receive spoken information from a user and convert it to usable digital information. Audio codec 1260 may likewise generate audible sound for a user, such as through a speaker, e.g., in a handset of device 1250. Such sound may include sound from voice telephone calls, may include recorded sound (e.g., voice messages, music files, etc.) and may also include sound generated by applications operating on device 1250.

The computing device 1250 may be implemented in a number of different forms, as shown in the figure. For example, it may be implemented as a cellular telephone 1280. It may also be implemented as part of a smartphone 1282, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms "machine-readable medium" "computer-readable medium" refers to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network ("LAN"), a wide area network ("WAN"), peer-to-peer networks (having ad-hoc or static members), grid computing infrastructures, and the Internet.

The computing system can include clients and servers. A client and server are generally remote from each other and typically interact through a communication network. The relationship of client and server arises by virtue of computer programs running on the respective computers and having a client-server relationship to each other.

EXAMPLE IMPLEMENTATION

Overview

This example pertains to an artificial-intelligence ("AI")-based study that was developed according to techniques described in this specification to detect, with high fidelity, patients with asymptomatic low left-ventricular dysfunction (ALVD) using non-invasive ten seconds digital ECG.

Background. ALVD is present in 2-9% of the population, associated with reduced quality of life and longevity, and is generally treatable when detected. The area under the curve (AUC) for a BNP screening blood test is 0.79 to 0.89. This study hypothesized that use of artificial intelligence (AI) would enable the ECG, a ubiquitous, inexpensive test, to identify left ventricular systolic dysfunction.

Methods. The study involved training a convolutional neural network using digitally stored 12 lead ECG and echocardiogram pairs from 44,959 patients from the MAYO CLINIC data vault to identify patients with ventricular dysfunction, defined as an ejection fraction (EF)≤35%. The network was then tested on 52,870 patients reserved for external validation.

Results. Of the 52,870 patients tested, 4,131 (7.8%) had an EF≤35%. The AUC of the ROC was 0.93. The sensitivity, specificity and accuracy were 86.3%, 85.7% and 85.7%, respectively. In 1335 patients with an abnormal AI screen but normal EF (false positives), 147 (11%) had at least one abnormal EF in the future (5 year incidence 9.5%). This four-fold increased risk of developing a future low LVEF suggests that the network may be detecting early, subclinical, metabolic or structural abnormalities that manifest in the ECG.

Conclusions. Applying artificial intelligence to the ECG—a ubiquitous and typically low cost test—permits the ECG to serve as a powerful tool to screen for left ventricular dysfunction and furthermore to identify individuals at increased risk for its development in the future.

Methods

Figure 13:
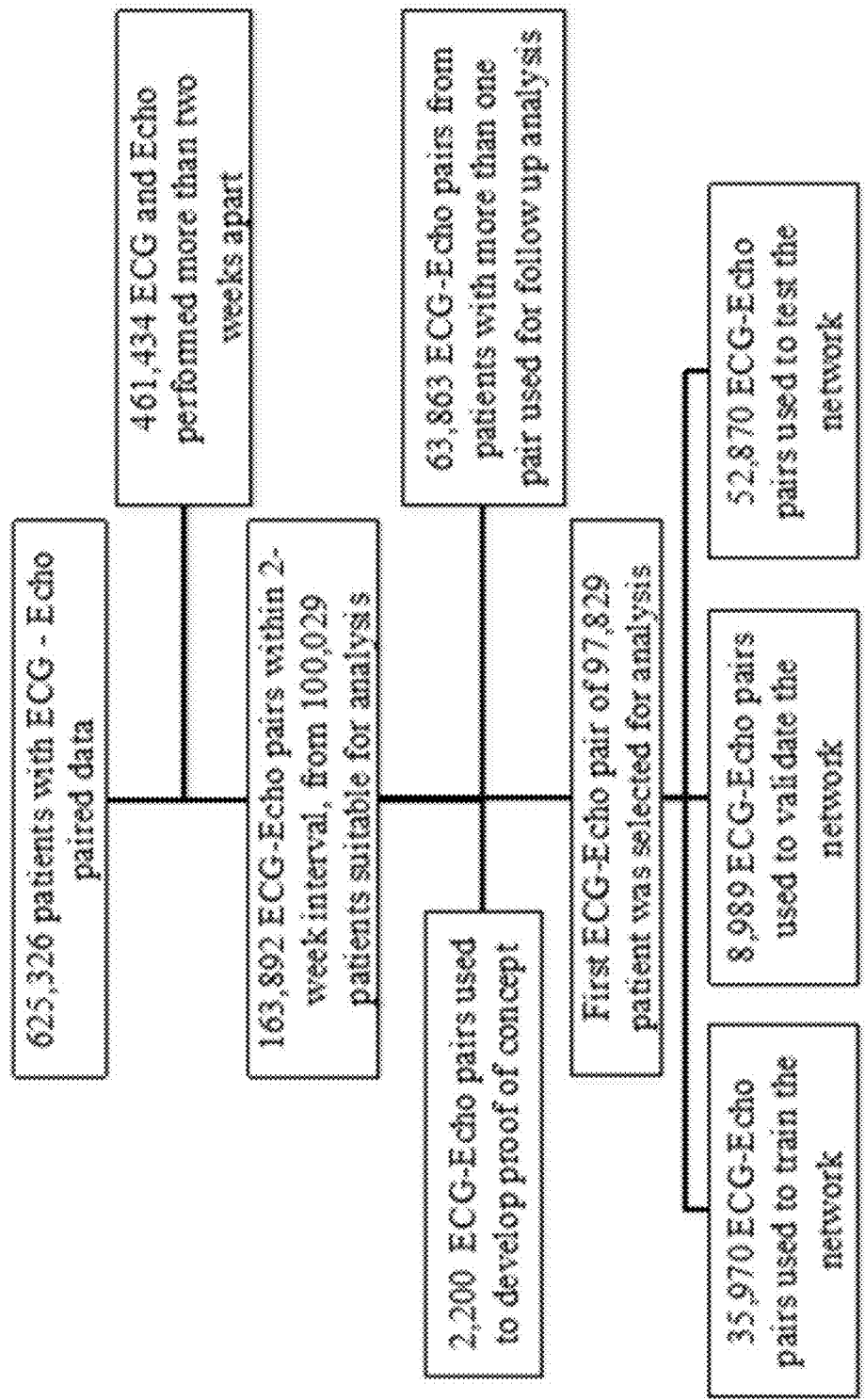
FIG. 13 is a chart representing the data mining schema for training, validating, and testing of a convolutional neural network ejection-fraction prediction model. To avoid cross contamination between datasets and network training based on the ECGs of specific patients, the ECG for each patient was used only once (and only in one of the groups). Patients with more than one data point were used for the follow-up analysis.

Data Sources and Study Population. Following institution review board approval, the study obtained data from the MAYO CLINIC digital data vault. 163,892 adult patients (18 years or older) were identified with at least one digital, standard 10-second 12-lead ECG acquired in the supine position between January 1994 and February 2017 and at least one transthoracic echocardiogram (TTE) obtained within 14 days of the index ECG (FIG. 13). For patients with multiple ECG and TTE data sets meeting these criteria, the earliest pair was used for network creation, validation, or testing, and subsequent TTE data used for analysis of follow up. A preliminary proof of concept assessment was performed in order to obtain internal funding using 2200 ECG-TTE data pairs, which were excluded from the present analysis, leaving a cohort of 97,829 patients whose first ECG-TEE paired data sets were used for the primary analysis.

ECGs were acquired at a sampling rate of 500 Hz using a GENERAL ELECTRIC-MARQUETTE ECG machine (Marquette, W I) and stored using the MUSE data management system for later retrieval. Comprehensive two-dimensional or three-dimensional and Doppler echocardiography was available in all patients. Quantitative data were recorded at the time of the acquisition in a MAYO CLINIC developed, custom database (Echo Image Management System, EIMS). Left ventricular ejection fraction (EF) is routinely measured or estimated using standardized methodologies, and in most reports, more than one value may be recorded. For the purpose of this study, the ejection fraction value used in the models was the first available from a standard hierarchical sequence: EF determined using 3-dimensional echocardiography (Yamani H, Cai Q, Ahmad M. Three-dimensional echocardiography in evaluation of left ventricular indices. Echocardiography 2012; 29:66-75), a biplane approach using the Simpson method, a two-dimensional method (Quinones M A, Waggoner A D, Reduto L A, et al. A new, simplified and accurate method for determining ejection fraction with two-dimensional echocardiography. Circulation 1981; 64:744-53), M-Mode, and in the absence of any of the preceding, the reported visually estimated EF. If the estimation was a range, the midpoint was used as a single EF value. Left ventricular EF was classified as low (≤35%, mildly depressed (35-49%) or normal (≥50%).

Primary and Secondary Outcomes. The primary outcome was the ability of the AI network to identify patients with a LVEF of 35% or less using the ECG signal alone. This value was selected due to its clear-cut clinical and therapeutic importance (Russo A M, Stainback R F, Bailey S R, et al. ACCF/HRS/AHA/ASE/HFSA/SCAI/SCCT/SCMR 2013 appropriate use criteria for implantable cardioverter-defibrillators and cardiac resynchronization therapy: a report of the American College of Cardiology Foundation appropriate use criteria task force, Heart Rhythm Society, American Heart Association, American Society of Echocardiography, Heart Failure Society of America, Society for Cardiovascular Angiography and Interventions, Society of Cardiovascular Computed Tomography, and Society for Cardiovascular Magnetic Resonance. J Am Coll Cardiol 2013; 61:1318-68). The secondary outcome was the ability of the AI network to identify individuals with a normal EF at the time of screening, but with an increased risk of subsequent low EF during follow up.

Overview of AI Model Development. The study involved developing a convolutional neural network (CNN) using the KERAS Framework with a TENSORFLOW (GOOGLE, Mountain View, CA) backend and PYTHON (van Rossum G. Python tutorial, Technical Report CS-R9526. Amsterdam 1995 May). CNNs, which have been applied to images (or videos), operate such that the convolutions can be used to extract very subtle patterns in a data set. Each 12-lead ECG was considered a 12×5000 (i.e., 12 leads by 10 seconds duration sampled at 500 Hz) "image" (van Rossum G. Python tutorial, Technical Report CS-R9526. Amsterdam 1995 May). The network was composed of N single lead convolutional layers, each of which was followed by a non-linear "Relu" activation function, a batch-normalization layer (Ioffe S, Szegedy C. Batch normalization: accelerating deep network training by reducing internal covariate shift International Conference on Machine Learning2015) and a max pooling layer (Nagi J, Ducatelle F, Di Caro G, et al. Max-pooling convolutional neural networks for vision-based hand gesture recognition. 2011 IEEE International Conference 2011:342-7). The features extracted from each raw, digital signal ECG lead were fused in another convolutional layer that had access to all leads simultaneously. Following the last convolutional layer, the data were fed to a fully connected network with two hidden layers with dropout layers to avoid overfitting and an output layer that was activated using the "Softmax" function (Cristianini N, Shawe-Taylor J. New York, NY: Cambridge University Press; 1999).

AI Model Training. Due to the large size of our data set, approximately 50% of the dataset was used for training the network. This left us with a very large data set to test the network to better assess its robustness (FIG. 13). After the initial split into the development and testing (holdout) datasets, the development dataset was further divided into the training data (80% of the development set) and the internal validation data (20%).

For training, ECGs were fed to the network and the network weights updated using the Adam optimizer (Kingma D P, Ba J. Adam: A Method for Stochastic Optimization 2014) with binary cross entropy as the loss function. After each epoch, the network was tested using the internal validation dataset and training was stopped after it was optimized. The network hyper-parameters were also tuned during this process, and the network with the lowest loss value was selected. All ECGs were low pass filtered (100 hz) to remove high frequency noise and quantization error.

Primary Outcome—AI Augmented ECG to Identify a Low EF. After selecting the optimal network using validation data, a receiver-operator curve (ROC) was created using the same validation set and measured its area under the curve (AUC) as primary assessment of network strength. The validation data set ROC was used to select two thresholds for the probability of having a low LVEF: The first was selected by giving an equal weight to sensitivity and specificity and the second selected yield a sensitivity of 90% on the validation dataset. The CNN model was then used on the test data to test its ability to predict a low LVEF. The two thresholds were used to calculate sensitivity, specificity and accuracy in the test data, which had not been used for model training or threshold selection. The impact of age and sex on network predictive function was also assessed by creating a separate network with those variables as inputs, and also by training a network to determine whether it could determine age and sex from the ECG alone.

Secondary Outcome—AI Augmented ECG to Predict a Future Low EF. It was hypothesized that early in the course of any disease that impacts EF, ECG signals would show subtle abnormal patterns due to metabolic and structural derangements that had not impacted a sufficient quantity of myocardium to cause a reduction in EF. It was further hypothesized that the CNN would classify some of these cases as abnormal, giving the initial appearance of a false positive test, that with time would become a true positive test. To test this hypothesis, a substudy was designed to identify patients that met the following conditions: 1) the network predicted the patient had a low EF; 2) the patient had an echocardiogram performed within 14 days that demonstrated a normal EF (≥50%) indicating a false positive finding by the algorithm; and 3) the patient had at least one additional echocardiogram (not used for training or testing) available at a future date. A control group was created using the true negative cases (algorithm and clinical determinations were both consistent with not having a low EF). For the control group, the subjects were selected to have LVEF≥50%. A Kaplan-Meier analysis was used to depict the incidence of low EF for the true negatives vs. the false positives over time. Subsequently, Cox proportional hazards regression was used to estimate the hazard for low EF after adjusting for age and sex. In addition, a sensitivity analysis was conducted by categorizing the predicted probability for low EF to determine if there was a monotonic pattern of the predicted probability with the development of future low EF.

Statistical Considerations. For measures of diagnostic performance (AUC ROC, sensitivity), the sample sizes are so large that normal confidence intervals (CIs) are expected to have a width of <0.5%. As such, the CIs are not reported alongside with the estimated values due to their high precision. Continuous data are presented as mean+/−SD. Cox models are presented with two-sided p-values. Survival analyses were conducted using SAS version 9.4. The CNN was trained using KERAS (version 2.0.3) and TENSORFLOW (version 1.0.1).

Study Support. The study was conceived, funded, and executed entirely by MAYO CLINIC. There was no industry support of any kind.

Results

Study Population. A total of 625, 326 patients with ECG—TTE paired were screened to identify the study cohort selected for analysis (FIG. 13). The first ECG-TTE data pair from patients with ECG and echocardiogram performed within a 2 week interval comprised the analysis data set, which consisted of 97,829 patients, 35,970 in the training set, 8,989 in the validation set, and 52,870 in the holdout testing set. No patient was in more than one group (FIG. 13). The overall patient population had a mean age of 61.8+/−16.5 years, and 7.8% of the population had an EF≤35%. Table 1 shows patient characteristics for the training, validation, and test sets. In the testing dataset 4,131 (7.8%) patients had an EF of 35% or less, 6,740 patients (12.7%) had an LVEF higher than 35% and lower than 50%, and 41,999 patients (79.5%) had an LVEF of 50% or higher. Over 89% of the TTEs were performed within one day of the index ECG.

Figure 14:
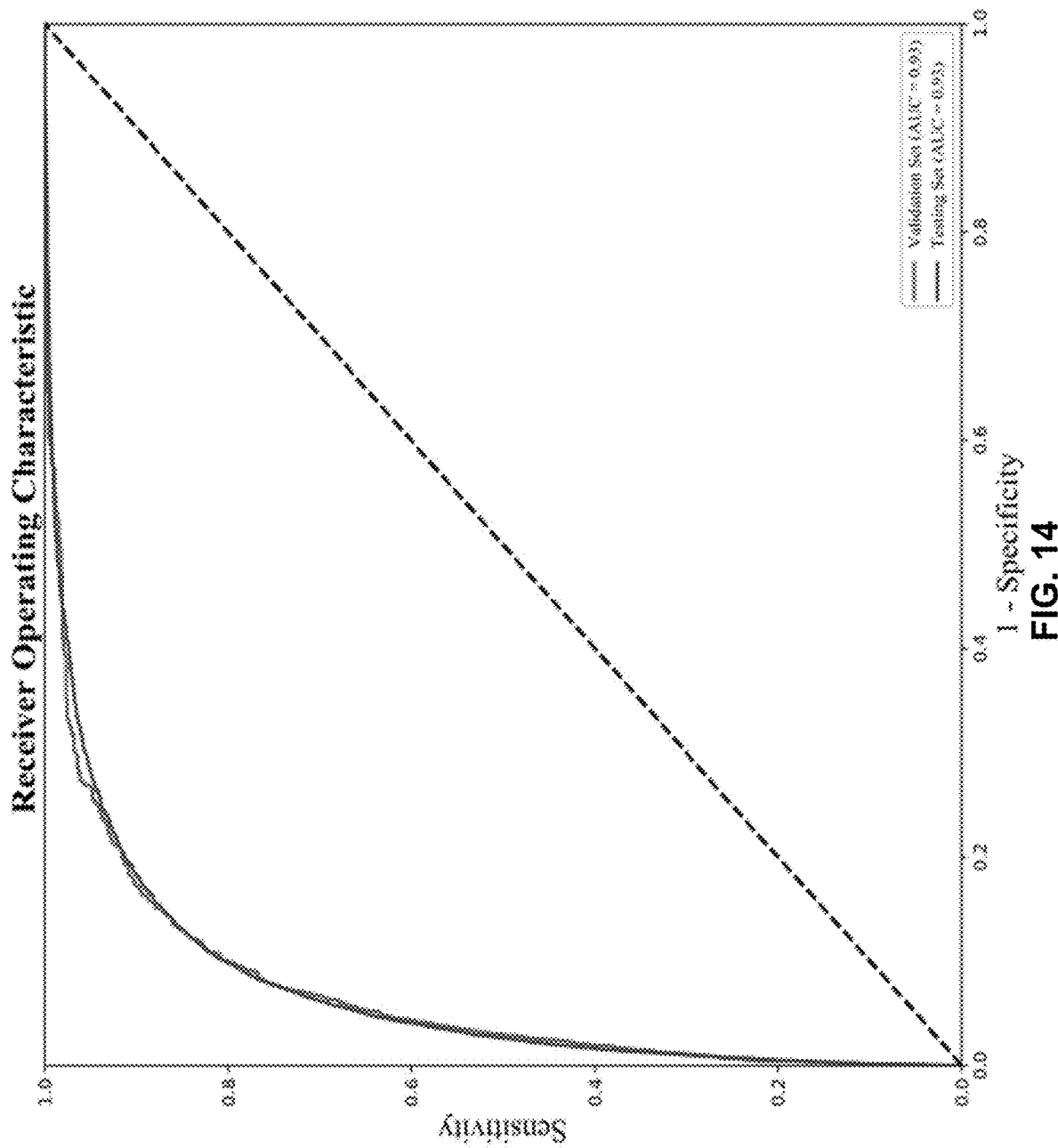
FIG. 14 depicts a receiver operating characteristic curve for use of the convolutional neural network to identify patients with an EF<=35%. The ROC and area under the curve (AUC) calculated using the validation and testing (holdout) datasets. The identical AUC demonstrates the robustness of the algorithm to different datasets.

Primary Outcome. The AUC of the holdout test dataset was 0.93 and was identical to the AUC of the internal validation dataset (0.93), FIG. 14. When selecting a threshold with no preference to sensitivity, the overall accuracy was 85.7% with a specificity of 85.7% and sensitivity of 86.3% and a negative predictive value of 98.7%. Using a threshold to yield a 90% sensitivity on the validation set and applying the algorithm to the testing dataset, the sensitivity was 89.1%, specificity 83%, overall accuracy 83.5%, and negative predictive value 98.9%. When patients with no known comorbidities (see FIG. 16) were separately analyzed by the network, the AUC increased to 0.98, with a sensitivity of 95.6%, specificity of 92.4%, negative predictive value of 99.8% and accuracy of 92.5%.

The network performance was not improved by additional inputs of age and sex. To understand whether the network was "determining" age and sex based on the ECG alone, the network was retrained to predict age and sex from the ECG. Age was predicted to 8.7+/−6 years and sex was accurately determined from the ECG 87% percent of the time with an AUC of 0.94. This indicated that the network could reliably determine age and sex from the ECG alone, explaining why its performance was not affected by age or sex, as it could compensate for these variables.

Figure 17:
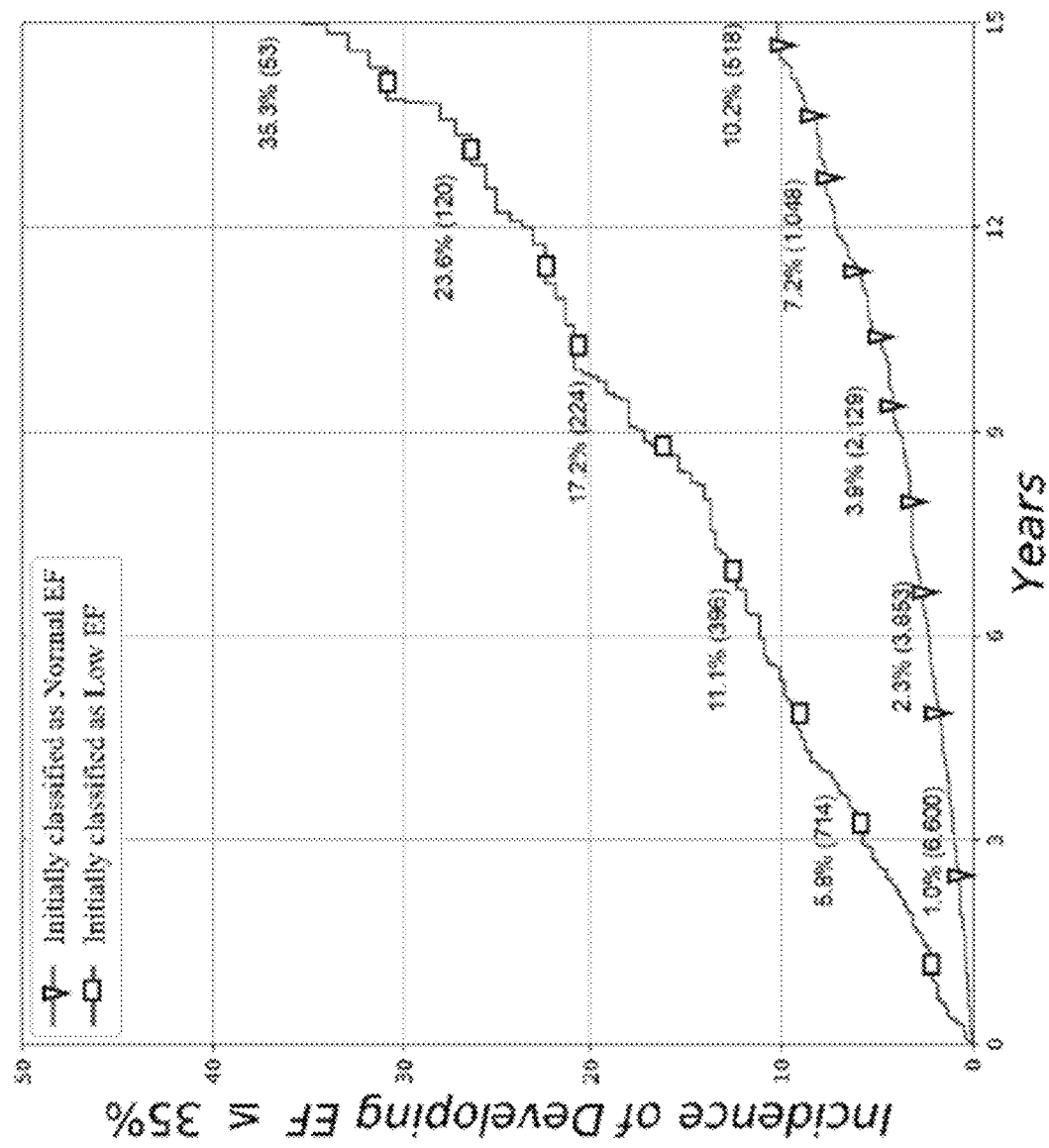
FIG. 17 plots the long-term outcome of patients with an EF>=50% at the time of initial classification. Patients with an initially normal EF who were classified at low EF by the network had a significantly increased risk of future LV dysfunction, compared to patients with normal EF classified as normal.

Distribution of EF Values by AI Algorithm Classification. When selecting a threshold with no preference to sensitivity (i.e. a threshold that will yield an equal sensitivity and specificity using validation data), 10,544 (19.9%) of patients in the test set were identified by the network as having a low EF. Of these 10,544 patients, 33.8% had an EF of 35% or less, 29.5% had an EF of 36-50% and 36.6% had a normal EF. In the group that the network identified as normal, 1.3% had an EF of 35% or lower and 8.6% had LVEF of 36-50%; the rest (90.1%) had a normal LVEF (FIG. 17).

Secondary Outcome—AI Augmented ECG to Predict a Future Low EF. Of the patients identified by the network as having a normal EF who also had a confirmatory normal contemporaneous EF by echocardiography ("true negative"), 11,515 had a follow up echocardiogram. Of these true negative patients, 302 developed a low EF over a median (IQR) follow up of 3.8 (1.4-7.5) years (FIG. 4: 4.4% 10 year incidence). In contrast, 1,335 patients were labelled by the network as having a low EF, but the contemporaneous echocardiogram demonstrated a normal EF ("false positive"). Of these 1,335 patients with an initial "false positive" result, 147 (FIG. 4: 20.8% 10 year incidence) developed left ventricular dysfunction during a median 3.4 (IQR 1.2-6.8) years follow up. This represented a 4-fold risk of future low EF when the AI algorithm defines the ECG as abnormal (age and sex adjusted HR=4.1 [3.3-5.0], p<0.001), suggesting the network identified ECG abnormalities before overt ventricular dysfunction became manifest.

Discussion

Left ventricular systolic dysfunction is associated with impaired quality of life, increased morbidity, and increased mortality (McDonagh T A, McDonald K, Maisel A S. Screening for asymptomatic left ventricular dysfunction using B-type natriuretic Peptide. Congest Heart Fail 2008; 14:5-8). The major cardiovascular professional societies have endorsed evidence-based therapies that improve symptoms and survival once it is detected (Al-Khatib S M, Stevenson W G, Ackerman M J, et al. 2017 AHA/ACC/HRS Guideline for Management of Patients With Ventricular Arrhythmias and the Prevention of Sudden Cardiac Death: Executive Summary: A Report of the American College of Cardiology/American Heart Association Task Force on Clinical Practice Guidelines and the Heart Rhythm Society. Circulation 2017; Yancy C W, Jessup M, Bozkurt B, et al. 2013 ACCF/AHA guideline for the management of heart failure: a report of the American College of Cardiology Foundation/American Heart Association Task Force on Practice Guidelines. J Am Coll Cardiol 2013; 62:e147-239). However, effective screening for ventricular dysfunction is lacking (McDonagh T A, McDonald K, Maisel A S. Screening for asymptomatic left ventricular dysfunction using B-type natriuretic Peptide. Congest Heart Fail 2008; 14:5-8; Redfield M M, Rodeheffer R J, Jacobsen S J, Mahoney D W, Bailey K R, Burnett J C, Jr. Plasma brain natriuretic peptide to detect preclinical ventricular systolic or diastolic dysfunction: a community-based study. Circulation 2004; 109:3176-81). This study found that the application of artificial intelligence using a convolutional neural network to the standard 12 lead ECG—an inexpensive, widely available, common clinical test—enabled detection of left ventricular dysfunction with an AUC of 0.93. The performance of this test compares favorably with other common screening tests such as prostate specific antigen for prostate cancer (0.92), mammography for breast cancer (0.85), and cervical cytology for cervical cancer (0.70). In contrast to BNP, accuracy was not impacted by age or sex. Importantly, in addition to effectively identifying individuals with ventricular systolic dysfunction, the network also predicted who with initially normal LV function would go on to develop a low EF. Such patients with an abnormal network screen but a normal EF ("false positive"), had a four-fold increased risk of developing ventricular dysfunction over the next 5 years (10% risk at five years). This suggests the network detected early, subclinical, metabolic or structural abnormalities that manifest in the ECG.

Congestive heart failure afflicts over 5 million people and consumes over $30 billion in health care expenditures annually in the US alone (Heidenreich P A, Albert N M, Allen L A, et al. Forecasting the impact of heart failure in the United States: a policy statement from the American Heart Association. Circ Heart Fail 2013; 6:606-19; Mozaffarian D, Benjamin E J, Go A S, et al. Heart disease and stroke statistics—2015 update: a report from the American Heart Association. Circulation 2015; 131:e29-322). Early detection and prevention is a healthcare imperative. Asymptomatic left ventricular dysfunction affects>7 million Americans, and many more individuals globally. It was found that 6% of patient in our population had low EF, consistent with previous studies (McDonagh T A, McDonald K, Maisel A S. Screening for asymptomatic left ventricular dysfunction using B-type natriuretic Peptide. Congest Heart Fail 2008; 14:5-8). BNP and NT-BNP have been proposed for detection of left ventricular systolic dysfunction. Bhalla and associates assessed BNP to screen for systolic and diastolic dysfunction and found an AUC of 0.60 for BnP and 0.70 for NTproBNP with results improving with the addition of impedance cardiography to 0.70, and 0.73 (Bhalla V, Isakson S, Bhalla M A, et al. Diagnostic ability of B-type natriuretic peptide and impedance cardiography: testing to identify left ventricular dysfunction in hypertensive patients. Am J Hypertens 2005; 18:73S-81S). A MAYO CLINIC study from Olmsted county assessing individuals aged 45 and above found the AUC was higher for individuals with more severe (0.82 to 0.92) than any (0.51 to 0.74) systolic dysfunction. Moreover, optimal discriminatory levels for BNP varied with age and sex. In contrast, the study found excellent AI network performance invariant to age and sex. This was validated by creating a network that was able to determine patient age within 8+/−6.3 years and sex with an accuracy of 87% based on the ECG alone. Previous work has described age and sex associated changes with the ECG (Daly C, Clemens F, Lopez Sendon J L, et al. Gender differences in the management and clinical outcome of stable angina. Circulation 2006; 113:490-8; Khane R S, Surdi A D, Bhatkar R S. Changes in ECG pattern with advancing age. J Basic Clin Physiol Pharmacol 2011; 22:97-101; Kuo T B, Lin T, Yang C C, Li C L, Chen C F, Chou P. Effect of aging on gender differences in neural control of heart rate. Am J Physiol 1999; 277:H2233-9; Stramba-Badiale M, Locati E H, Martinelli A, Courville J, Schwartz P J. Gender and the relationship between ventricular repolarization and cardiac cycle length during 24-h Holter recordings. Eur Heart J 1997; 18:1000-6). During the training process, the network integrated age and sex characteristics to compensate for them so that they did not affect its discriminatory power for identifying ventricular dysfunction. This capability appears to be unique to the neural network screen.

The specific ECG characteristics used by the unsupervised convolutional neural network to classify individuals as having or lacking a low EF are not known, due to the nature of neural networks. However, by training the network with a large cohort of approximately 45,000 ECG and EF data pairs, the network was exposed to a sufficient number of electrocardiographic variants to classify with certainly individuals with a low ejection fraction, as demonstrated by the AUC of 0.93 when tested in a population of 52,870 individuals. In contrast to the previous application of neural networks in medicine to mimic human skills, such as with identification of mammographic lesions (Salazar-Licea L A, Pedraza-Ortega J C, Pastrana-Palma A, Aceves-Fernandez M A. Location of mammograms ROI's and reduction of false-positive. Comput Methods Programs Biomed 2017; 143:97-111), this study expands the use of AI to extend capacity beyond that of human skills.

An important characteristic of our network is that it uses an inexpensive, standardized, ubiquitous test as its input—the 12 lead ECG. In many rural areas in the United States (Gruca T S, Pyo T H, Nelson G C. Providing Cardiology Care in Rural Areas Through Visiting Consultant Clinics. J Am Heart Assoc 2016; 5) and in developing countries, access to cardiology care and imaging is limited. The availability of a portable, inexpensive, test for ventricular systolic dysfunction permits optimal utilization of limited imaging resources, enabling individuals to benefit from proven therapies such as beta adrenergic blockers, angiotensin receptor antagonists, and where available, implantable devices (defibrillators and cardiac resynchronization systems) (Yancy C W, Jessup M, Bozkurt B, et al. 2013 ACCF/AHA guideline for the management of heart failure: a report of the American College of Cardiology Foundation/American Heart Association Task Force on Practice Guidelines. J Am Coll Cardiol 2013; 62:e147-239; Yancy C W, Jessup M, Bozkurt B, et al. 2017 ACC/AHA/HFSA Focused Update of the 2013 ACCF/AHA Guideline for the Management of Heart Failure: A Report of the American College of Cardiology/American Heart Association Task Force on Clinical Practice Guidelines and the Heart Failure Society of America. J Am Coll Cardiol 2017; 70:776-803). With the emergence of smartphone-enabled electrodes (Yasin O Z, Attia Z, Dillon J J, et al. Noninvasive blood potassium measurement using signal-processed, single-lead ecg acquired from a handheld smartphone. J Electrocardiol 2017; 50:620-5), mobile applications may permit use in resource constrained geographies. The software-based nature of test "samples" for the network implemented in this study also enables continuous feedback and refinement, with rapid distribution of system improvements.

Figure 15:
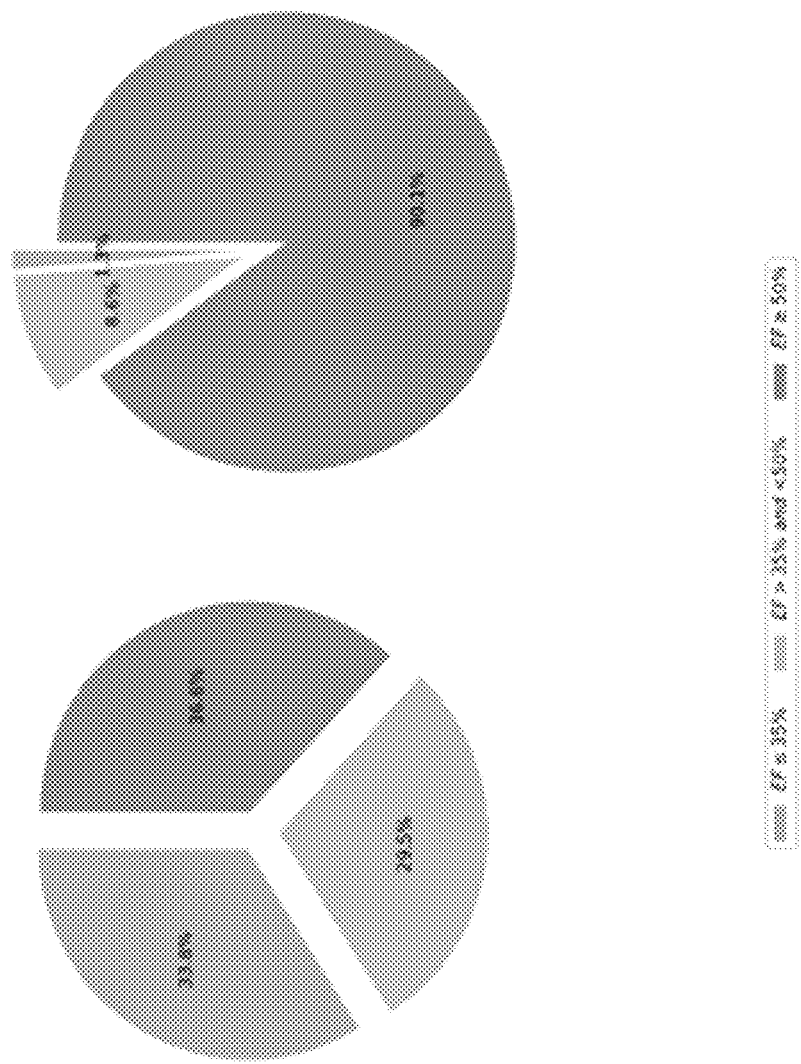
FIG. 15 provides pie charts showing the distribution of ejection-fraction based on network classification. Of patients classified as having a low ejection fraction, 63.5% had an ejection fraction under 50%. If classified as normal, 1.3% had an ejection fraction <=35%, and 90.1% had an EF>=50%

In this study, an EF of 35% or less was selected as the detection threshold due to the well-established outcome and therapeutic implications of this value (Yancy C W, Jessup M, Bozkurt B, et al. 2017 ACC/AHA/HFSA Focused Update of the 2013 ACCF/AHA Guideline for the Management of Heart Failure: A Report of the American College of Cardiology/American Heart Association Task Force on Clinical Practice Guidelines and the Heart Failure Society of America. J Am Coll Cardiol 2017; 70:776-803). However, identification of an EF under 50% is still clinically significant. Thus, 45% of the "false positive" values were actually clinically meaningful (FIG. 15). Additionally, the network can easily be configured to instead use a different detection threshold, for example, identification of an EF<40%. The ECG—TTE pairs were not simultaneously acquired. However, since the study included over 100,000 ECG-TTE paired data sets with over 89% of TTEs performed within 24 hours of the ECG, the likelihood of inaccuracy related to temporal delay is small. The convolutional neural network in this study was specifically trained to detect low EF—diastolic dysfunction and heart failure are not detected. However, evidence-based therapies that reduce morbidity and mortality are established for the treatment of low EF, which is at times asymptomatic, making its detection paramount.

Although a number of implementations have been described in detail above, other modifications are possible. In addition, the logic flows depicted in the figures do not require the particular order shown, or sequential order, to achieve desirable results. Other steps may be provided, or steps may be eliminated, from the described flows, and other components may be added to, or removed from, the described systems. Accordingly, other implementations are within the scope of the following claims.

What is claimed is:
1. A computer-implemented method, comprising:
receiving, by a system of one or more computers, electrocardiogram (ECG) data that describes an ECG of a first subject over a period of time;
processing, by the system, the ECG data to generate a predictive input;

providing, by the system, the predictive input to a prediction model:
    wherein the prediction model is an iteratively trained machine learning model, wherein the iteratively trained machine learning model comprises a convolutional neural network comprising a plurality of single lead convolutional layers and a convolutional layer that has access to each lead of the ECG;
processing the predictive input with the prediction model to generate a subject structural heart disease prediction for the first subject; and
providing, for output, the subject structural heart disease prediction for the first subject.

2. The method of claim 1, wherein processing the ECG data to generate a predictive input comprises:
    normalizing and vectorizing the ECG data from one or more channels; and
    generating the predictive input based on the normalized and vectorized ECG data.

3. The method of claim 1, wherein the predictive input comprises a series of values indicating an amplitude of the ECG data for at least one lead over one or more cardiac cycles.

4. The method of claim 1, wherein the predictive input comprises one or more values of one or more morphological features of the ECG data.

5. The method of claim 1, wherein the ECG data is from one or more channels, each of the one or more channels associated with one or more ECG leads.

6. The method of claim 1, further comprising estimating an ejection fraction value from the predictive input.

7. The method of claim 6, wherein the first prediction model processes the estimated ejection fraction value to generate a structural heart disease prediction.

8. The method of claim 1, wherein the subject structural heart disease prediction comprises a determination of a present or impending structural heart disease.

9. The method of claim 1, wherein the first prediction model is a regression model.

10. The method of claim 1, further comprising a notification service, the notification service pushing the subject structural heart disease prediction to a display for presentation to the first subject.

11. One or more non-transitory computer-readable media encoded with instructions that, when executed by one or more processors of a system, cause the one or more processors to perform operations comprising:
    receiving, by a system of one or more computers, electrocardiogram (ECG) data that describes an ECG of a first subject over a period of time;
    processing, by the system, the ECG data to generate a predictive input;
    providing the predictive input to a prediction model, wherein the prediction model is an iteratively trained machine learning model, wherein the iteratively trained machine learning model comprises a convolutional neural network comprising a plurality of single lead convolutional layers and a convolutional layer that has access to each lead of the ECG;
    processing the predictive input with the prediction model to generate a subject structural heart disease prediction for the first subject using the trained first prediction model; and
    providing, for output, the subject survival estimation prediction for the first subject.

12. A computer-implemented method, comprising:
    receiving, by a system of one or more computers, electrocardiogram (ECG) data that describes an ECG of a first subject over a period of time;
    processing, by the system, the ECG data to generate a predictive input;
    providing, by the system, the predictive input to a survival estimation model
        wherein the survival estimation model is an iteratively trained machine learning model, wherein the iteratively trained machine learning model comprises a convolutional neural network comprising a plurality of single lead convolutional layers and a convolutional layer that has access to each lead of the ECG;
    processing the predictive input with the survival-estimation model to generate a subject survival estimation prediction for the first subject; and
    providing, for output, the subject survival estimation prediction for the first subject.

13. The method of claim 12, wherein the first survival estimation model is a regression model.

14. The method of claim 13, wherein the first survival estimation model is a neural network.

15. The method of claim 14, wherein the neural network is a feedforward neural network, a convolutional neural network, or a recurrent neural network.

16. The method of claim 12, wherein the predictive input is a value of one or more morphological features of the ECG.

17. The method of claim 16, wherein the one or more morphological features include at least one of T-wave amplitude, P-wave amplitude, P-wave area, T-wave area, T-wave left slope, T-wave right slope, P-wave left slope, P-wave right slope, T-wave duration, P-wave duration, PR-interval, QRS duration, QRS amplitude, QRS area, QRS energy, QRS peak-to-peak ratio, or QT-segment length.

* * * * *